United States Patent [19]

Morrow et al.

[11] Patent Number: 5,166,062

[45] Date of Patent: Nov. 24, 1992

[54] METHODS FOR SEPARATING DIOL AND TRIOL STEREOISOMERS FROM A STEREOISOMER MIXTURE

[75] Inventors: Cary J. Morrow; Joe S. Wallace, both of Alburquerque, N. Mex.

[73] Assignee: University of New Mexico, Albuouerque, N. Mex.

[21] Appl. No.: 470,668

[22] Filed: Jan. 26, 1990

[51] Int. Cl.$^5$ .............................................. C12P 7/62
[52] U.S. Cl. .................................. 435/135; 435/134; 435/280
[58] Field of Search ........................ 435/134, 135, 280

[56] References Cited

PUBLICATIONS

Wang, Y. F. et al., "Extending the Applicability of Esterases of Low Enantioselectivity in Asymmetric Synthesis", *Enzymes in Organic Synthesis*, Pittman, London pp. 128–145 1985.
Bianchi, D. et al., "Anhydrides as Acylating Agents in Lipase–Catalyzed Stereoselective Esterification of Racemic Alcohols", J. Org. Chem., vol. 53, pp. 5531–5334, 1988.
Koppenhoefer et al, J. Chromatog. 358:159 (1986).
Hemmerle et al, Tetrahedron Lett. 28:3471 (1987).
Ramos Tombo et al, Tetrahedron Lett. 27:5707 (1986).
Huang et al, J. Am. Chem. Soc. 97:14 (1975).
Chen et al, J. Sm. Chem. Soc. 103:3580 (1981).
Cambou et al, J. Am. Chem. Soc. 107:2687 (1984).
Zaks et al, Science 224:1249 (1984).
Gatfield, Annals N.Y. Acad. Sci. 568:(1984).
Zaks et al, PNAS (USA) 82:3192 (1985).
Klibanov, CHEMTECH 354 (1986).
Cambou et al, Biotechnology and Bioengineering 26:1449 (1984).
Kirchner et al, J. Am. Chem. Soc. 107:2072 (1985).
Langard et al, Tetrahedron Lett., 26:1857 (1985).
Langrand et al, Tetrahedron Lett., 27:29 (1986).
Gil et al, Tetrahedron Lett., 28:1647 (1987).
Bianchi et al, J. Org. Chem. 53:5531 (1988).
Francalanci et al, J. Org. Chem. 52:5079 (1987).

*Primary Examiner*—Douglas W. Robinson
*Assistant Examiner*—Marian C. Knode
*Attorney, Agent, or Firm*—Lowe, Price, LeBlanc & Becker

[57] ABSTRACT

Methods of separating the stereoisomers of secondary di- and tri-alcoholic compounds comprise reacting a racemic mixture of the secondary alcohols with an acyl anhydride or an ester in the presence of an enzyme which stereoselectively acylates the (R) site of the alcohol to form the (R) site acyl ester of the alcohol and separating the (S,S) or (S,S,S) secondary alcohol, the (R,S) or (R,S,S) monoacyl ester of the alcohol, the (R,R) or (R,R,S) diacyl ester and/or the (R,R,R) triacyl ester of the alcohol from one another and from the reaction medium. Additional methods of separating the stereoisomers of a secondary di- or tri-alcohol comprise reacting a stereochemical mixture of acyl esters of the di- or tri-alcohol with an enzyme which selectively deacylates the (R) or (S) site of the secondary alcohol to produce (R) or (S) site deacylated isomers of the secondary alcohol and separating the free alcohol, the monoacyl ester, the diacyl ester, and the triacyl ester of the alcohol from one another and the reaction medium.

16 Claims, No Drawings

METHODS FOR SEPARATING DIOL AND TRIOL STEREOISOMERS FROM A STEREOISOMER MIXTURE

TECHNICAL FIELD

This invention relates to stereochemically pure diols and triols which are valuable intermediates in the preparation of polymers, acetals and crown ethers. This invention also relates to methods of preparing the stereochemically pure compounds disclosed herein.

BACKGROUND ART

Diols are valuable intermediates in the preparation of polymers, acetals, and crown ethers, and optically active diols, in particular, have been widely used for stereochemical control in homochiral syntheses. Unfortunately, the number of optically active diols, other than those associated with carbohydrates is quite small. Thus, a general source of optically active diols could provide valuable new building blocks for many structures.

Most techniques for the preparation of optically active diols focus on the stereospecific synthesis of a single enantiomer. The chemicals for preparing both enantiomers via such a procedure are not always available. In addition, in many cases, the stereochemistry at the second chiral center is determined by that at the first, limiting the allowable distance between the two. Finally, a completely different approach is generally required for preparing the meso stereoisomer.

An efficient method for the preparation of all possible stereoisomers of symmetric, secondary diol monomers would allow, for example, the synthesis of an all (R), an all (S) or an (R,S) "pseudo-syndiotactic" polymer as well as polymers containing any combination of the above stereochemistries. While the separation of stereoisomers can be achieved by vapor phase chromatography (VPC) (Koppenhoefer, B.; Walswer, M.; Bayer, E.; Abdalla, S., *J. Chromatog.*, 1986, 358, 159), such a method is, strictly speaking, not useful on a preparative scale.

Hydrolase enzymes specific for diol stereochemistry have been exploited for some time. However, their use has been limited to the modification of one chiral center in a meso diol (or diacetylated meso diol) (Hemmerle, H., Gais, H. J, *Tetrahedron Lett.*, 1987, 28, 3471), or to the modification of a specific hydroxyl (or esterified hydroxyl) of a diol bearing a prochiral center (Ramos Tombo, G. M.; Schar, H. P.; Fernandez i Busquets, X.; Ghisalba, O., *Tetrahedron Lett.*, 1986, 27, 5707).

Early examples of using enzymes to hydrolyze one of a pair of like groups involved the stereoselective hydrolysis of one of a pair of esters in aqueous media (Huang, F. C.; Lee, L. F. H.; Mittal, R. S. D.; Ravikumar, P. R.; Chan, J. A.; Sih, C. J.; Caspi, E.; Eck, E. R., *J. Am. Chem. Soc.*, 1975, 97, 4144; Ohno, M.; Kobayashi, S.; Limori, T.; Wang, Y. F.; Izawa, T., *J. Am. Chem. Soc.*, 1981, 103, 2405; Chen, C. S.; Fujimoto, Y.; Sih, C. J., *J. Am. Chem. Soc.*, 1981, 103, 3580). The recent discovery, however, (Cambou, B.; Klibanov, A. M., *J. Am Chem. Soc.*, 1984, 106, 2687; Zaks, A.; Klibanov, A. M., *Science*, 1984, 224, 1249; Gatfield, I. L., *Annals N. Y. Acad. Sci.*, 1984, 568; Zaks, A.; Klibanov, A. M., *Proc. Natl. Acad. Sci U.S.A.*, 1985, 82, 3192; Klibanov, A. M., *CHEMTECH*, 1986, 354) that such enzymes are also effective catalysts in low to moderate polarity organic solvents has allowed the development of esterification and transesterification as viable, alternative processes, enzymes can carry out (Cambou, B.; Klibanov, A. M., *Biotechnology and Bioengineering*, 1984, XXVI, 1449; Kirchner, G.; Scollar, M. P.; Klibanov, A. M., *J. Am. Chem. Soc.*, 1985, 107, 7072; Langrand, G.; Secchi, M.; Buono, G.; Baratti, J.; Triantaphylides, C., *Tetrahedron Lett.*, 1985, 26, 1857; Langrand, G.; Baratti, J.; Buono G.; Triantaphylides, C., *Tetrahedron Lett.*, 1986, 27, 29; Gil, G.; Ferre, F.; Meou, A.; Le Petit, J.; Triantaphylides, C., *Tetrahedron Lett.*, 1987, 28, 1647; Bianchi, D.; Cesti, P.; Battistel, E., *J. Org. Chem.*, 1988, 53, 5531; F.; Cesti, P.; Cabri, W.; Bianchi, D.; Martinengo, T.; Foa, *J. Org. Chem.*, 1987, 52, 5079).

In a typical organic phase resolution, the enzyme catalyzes the reaction of an activated ester with one enantiomer of a racemic alcohol. When the reaction has reached approximately 50% completion, it is stopped by filtering out the enzyme catalyst. The products of interest are an unchanged, optically active alcohol and an optically active ester. Following separation of the unchanged alcohol enantiomer from the ester, the latter can be hydrolyzed (chemically or enzymatically) to obtain the second enantiomer of the optically active alcohol.

In a modification of this procedure, Bianchi et al. have shown that acid anhydrides can be used with lipases in place of the activated ester to stereoselectively esterify chiral alcohols (Bianchi, D.; Cesti, P.; Battistel, E., *J. Org. Chem.*, 1988, 53, 5531). This method exhibits both high reaction rates and selectivities.

Because of the current interest in the preparation of optically active polymers, and due to a lack of feasible large-scale methods for the preparation of isolated stereoisomeric AA type monomers, there is still a need for simple, large-scale methods for the preparation of secondary diol monomers which result in high purity, stereochemically pure isomers which are substantially free of the remaining stereoisomers of the compound.

DISCLOSURE OF THE INVENTION

This invention relates to a compound of the formula

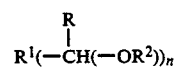

wherein
n is 2 to 3;
R and $R^1$ are different from one another and are selected from the group consisting of $(C_1-C_{20})$alkyl, alkenyl or alkynyl, $(C_3-C_{22})$cycloalkyl and $(C_4-C_{22})$aryl, wherein said alkyl, alkenyl, alkynyl, cycloalkyl and aryl may be substituted with N, O or S in the ring or chain structure and with $(C_1-C_4)$alkyl, alkenyl or alkynyl, halogen, $(C_1-C_{10})$alkoxy or aryloxy, $NO_2$ or $NHCOR^4$, wherein $R^4$ is H, $(C_1-C_6)$alkyl, alkenyl or alkynyl, which may be further substituted with S, N or O; and
$R^2$ is H or $(C_1-C_{20})$acyl or benzoyl which may be further substituted with N, S or O, and the alkyl and aryl residues thereof may be further substituted with CN, COOH, halogen, $HOOC(C_1-C_6)$alkyl, $HOOC(C_1-C_6)$alkenyl, $HOOC(C_1-C_6)$alkynyl or CO, said compound being in substantially stereochemically pure form.

This invention also relates to a polymer of the formula

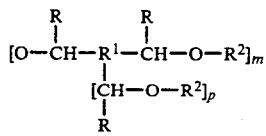

wherein
R and $R^1$ are different from one another and are selected from the group consisting of $(C_1-C_{20})$alkyl, alkenyl or alkynyl, $(C_3-C_{22})$cycloalkyl and $(C_4-C_{22})$aryl, said alkyl, alkenyl, alkynyl, cycloalkyl and aryl may be substituted with N, O or S in the ring or chain structure, and said alkyl, alkenyl, alkynyl, cycloalkyl and aryl may be further substituted with $(C_1-C_4)$alkyl, alkenyl or alkynyl, halogen, $(C_1-C_{10})$alkoxy or aryloxy, $NO_2$ or $NHCOR^4$, wherein $R^4$ is H, $(C_1-C_6)$alkyl, alkenyl or alkynyl, or $(C_4-C_{10})$ aryl which may be further substituted with N, S or O; and $R^2$ is selected from the group consisting of —CO—, CO—$R^3$—CO, $(CH_2)_q$, 1,2-, 1,3-, or 1,4-$(C_6H_4)$, 4,4'-biphenylene and OCNH—$R^3$—NHCO, wherein $R^3$ is $(C_1-C_{10})$alkyl, alkenyl or alkynyl or $(C_4-C_{20})$cycloalkyl, alkylaryl or aryl or

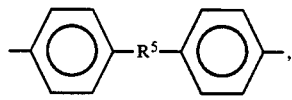

wherein $R^5$ is $(C_1-C_{10})$alkyl, alkenyl or alkynyl or $(C_3-C_{20})$ cycloalkyl or $(C_4-C_{14})$ aryl, all of which may be further substituted with N, S or O in the ring or chain structure and/or with halogen, $NO_2$ or $(C_1-C_4)$alkoxy;
q is 1 to 12;
m is 1 to 10,000; and
p is 0 to m.

Still part of this invention is a method of separating stereoisomers of the compounds of the invention, said method comprising
obtaining a stereochemical mixture of a secondary alcohol of the formula $R^1$—(—HC(—R)(—OH))$_n$, wherein n is 2 or 3, and R and $R^1$ are as described above;
reacting the alcohol mixture with an $R^7$ acyl anhydride or a $R^6OCOR^7$ ester, wherein $R^6$ is $(C_1-C_4)$-alkyl, $CF_3CH_2$, $CCl_3CH_2$, nitrophenyl or chlorophenyl, and $R^7$ is $(C_1-C_5)$alkyl, $CH_2Cl$, or $CH_2CN$, in the presence of an enzyme capable of stereoselectively acylating the (R) site (or the (S) site) of a secondary alcohol, said alcohol mixture, anhydride (or activated ester) and enzyme being provided in a medium, in proportions and under conditions effective to form an (R) site(s) (or (S) site(s)) acyl ester(s) of the secondary alcohol; and
separating the (S,S) or (S,S,S) (or (R,R) or (R,R,R)) secondary alcohol, the (R,S) or (R,S,S) (or (R,R,S)) monoacyl ester of the secondary alcohol and the (R,R) or (R,R,S) (or (S,S) or (R,S,S)) diacylester or the (R,R,R) (or (S,S,S)) triacyl ester of the secondary alcohol stereoisomers from one another and from the reaction medium.

Also part of this invention is a further method of separating the stereoisomers of the compounds of the invention, said method comprising
obtaining a stereochemical mixture of secondary alcohol esters of the formula $R^1$(—CH(—R)(—OR$^2$))$_n$, wherein n is 2 or 3, and R and $R^1$ are as described above, and $R^2$ is $(C_1-C_7)$acyl;
reacting the stereochemical mixture of esters with an enzyme capable of selectively deacylating the (R) site (or the (S) site(s)) of a secondary alcohol, said ester and enzyme being provided in an aqueous or partially aqueous medium in a proportion and under conditions effective to produce (R) (or (S)) site deacylated isomers of the secondary alcohol; and
separating the (R,R,R) or (R,R) (or (S,S,S)) or (S,S)) free alcohol, the (R,R,S) or (R,S) (or (R,S,S)) monoacyl ester, the (R,S,S) or (S,S) (or (R,R,S) or (R,R)) diacylester and/or the (S,S,S) (or R,R,R) triacyl ester stereoisomers of the alcohol from one another and from the reaction medium.

A more complete appreciation of the invention and many of the attended advantages thereof will be readily perceived as the same becomes better understood by reference to the following detailed description. Other objects, advantages and features of the present invention will become apparent to those skilled in the art from the following discussion.

BEST MODE FOR CARRYING OUT THE INVENTION

This invention arose from a desire to provide a simple, large-scale method for the preparation of symmetric, secondary diol monomers in stereochemically pure form and high yield. The present approach encompasses a combination of enzymatic and chemical steps which permit the separation of a stereoisomer mixture of the symmetric, secondary diol monomers in a clean and simple manner.

The enzymatic and chemical steps may be repeated more than once on partially separated diols to attain a separation of higher stereochemical purity. The present methods base the separation of the stereoisomers of a stereoisomer mixture on the ability of an enzyme to distinguish the stereochemistry at each chiral center of the substrate without regard to the presence or absence of other chiral centers in the molecule. In addition, the present methods also rely on the different characteristics of alcohols and their esters for the separation of the different stereoisomers.

The novel compounds have the general formula $$R^1(-CH(-OR^2)(-R))_n$$

wherein
n is 2 to 3;
R and $R^1$ are different from one another and are selected from the group consisting of $(C_1-C_{20})$alkyl, alkenyl or alkynyl, $(C_3-C_{22})$cycloalkyl and $(C_4-C_{22})$aryl, wherein said alkyl, alkenyl, alkynyl, cycloalkyl and aryl may be substituted with N, O or S in the ring or chain structure and with $(C_1-C_4)$alkyl, alkenyl or alkynyl, halogen, $(C_1-C_{10})$- alkoxy or aryloxy, $NO_2$ or $NHCOR^4$, wherein $R^4$ is H, $(C_1-C_6)$alkyl, alkenyl or alkynyl or $(C_4-C_{10})$aryl which may be further substituted with N, S or O; and
$R^2$ is H or $(C_1-C_{20})$acyl or benzoyl, which may be further substituted with N, S, or O, and the alkyl or aryl residues thereof may be further substituted with CN, COOH, halogen, $HOOC(C_1-C_6)$alkyl, $HOOC(C_1-C_6)$alkenyl, $HOOC(C_1-C_6)$alkynyl or CO; said compound being in substantially stereochemically pure form.

The compounds provided by this invention are up to about 95% free of other stereoisomers, and in some instances, more than about 95%, and even more than about 97% free of their stereoisomers and in some instances may contain no detectable quantity of their stereoisomers.

Preferred groups of compounds are those where R is $(C_1-C_{10})$alkyl, $R^2$ is H, or $R^1$ is benzene, biphenylene or pyridine. Other preferred groups of compounds are those wherein the R and $R^1$ groups are further substituted with alkyl, alkenyl or alkynyl, halogen, alkoxy or aryloxy, $NO_2$ or $NHCOR^4$, wherein $R^4$ is as described above. Another preferred group is that where $R^2$ encompasses $(C_1-C_6)$acyl substituents. Still another preferred group is that wherein $R^2$ is acyl which is further substituted with halogen, N, HOOC, $HOOC(C_1-C_6)$alkyl, $HOOC(C_1-C_6)$alkenyl, $HOOC(C_1-C_6)$alkynyl, or CO.

In one of the preferred embodiments, $R^1$ is 1,4-phenyl, 1,3-phenyl, 4,4'-biphenylyl or 2,6-pyridinyl.

Another preferred group is that where n is 2 and the compound is selected from the group consisting of the (R,R), (R,S), and (S,S) stereoisomers thereof.

Typical examples of the symmetric, secondary diol monomers are the following.

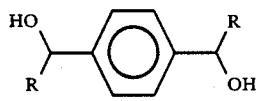

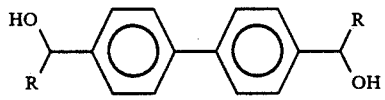

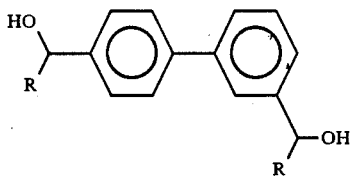

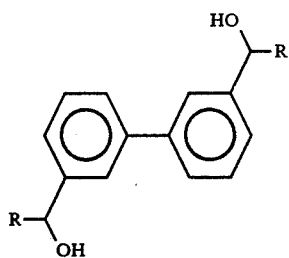

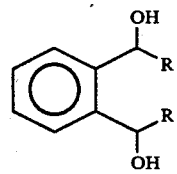

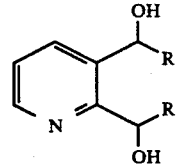

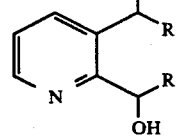

-continued

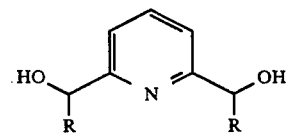

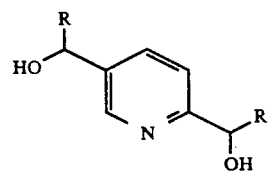

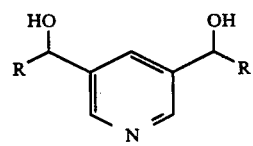

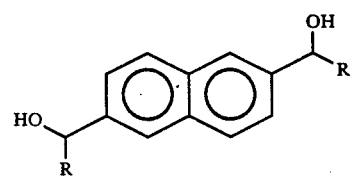

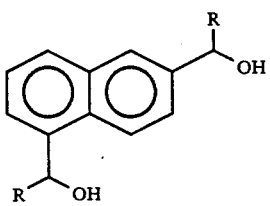

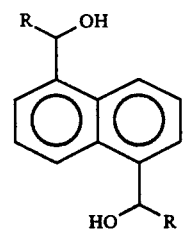

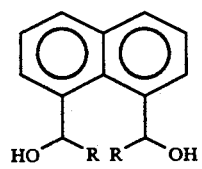

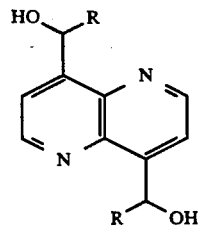

-continued
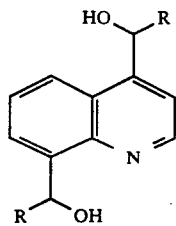
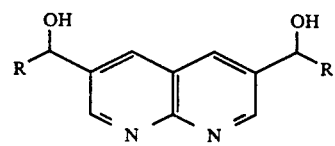
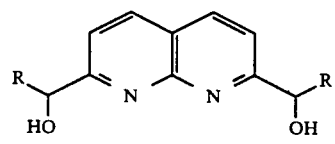
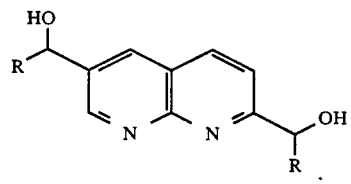
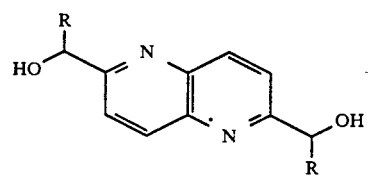
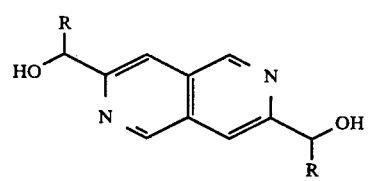
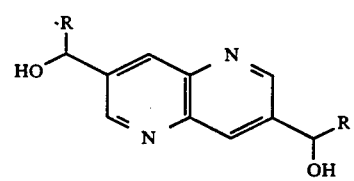
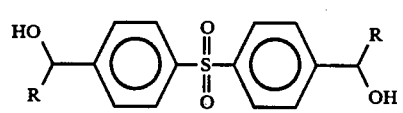
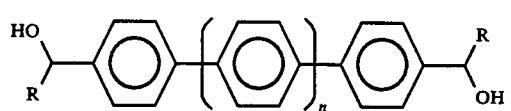
n = 1, 2, 3
-continued
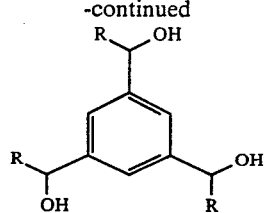
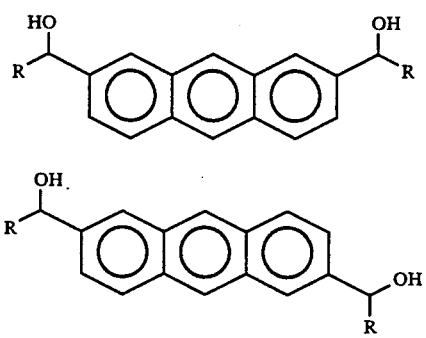
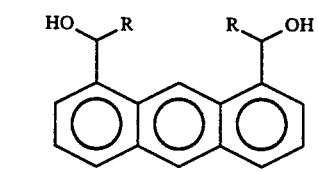
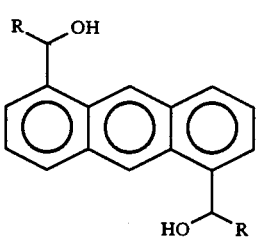
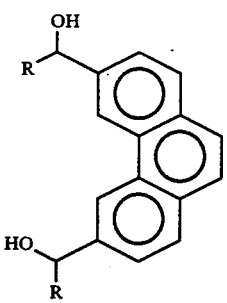
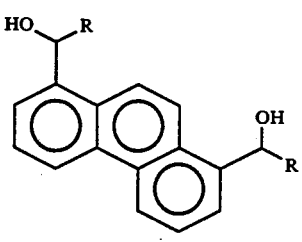

-continued
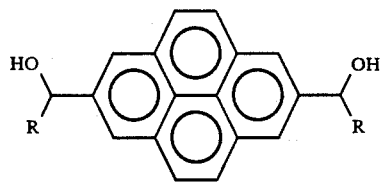
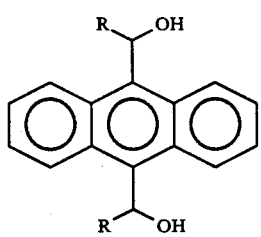
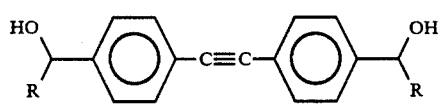
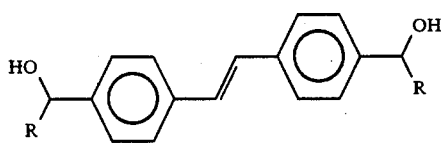
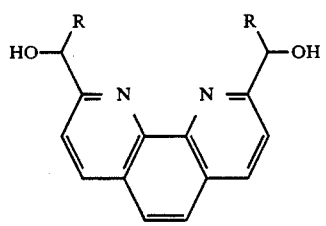
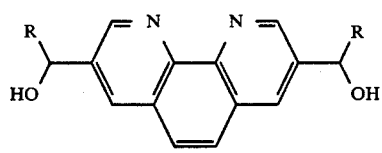
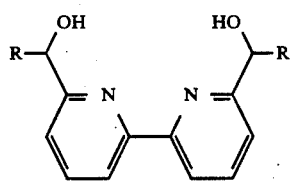
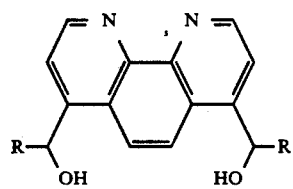
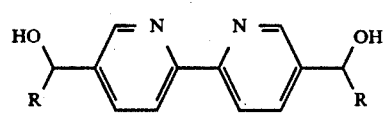
-continued
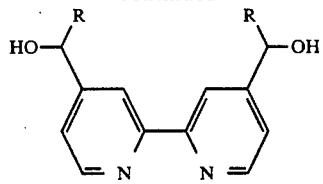
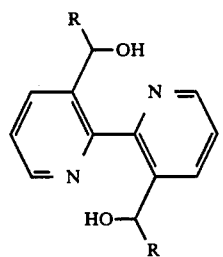
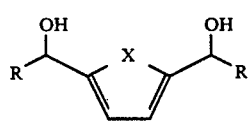
X = CH$_2$, O, S, NH
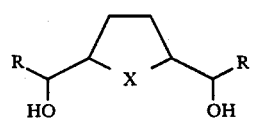
X = CH$_2$, O, S, NH, NR
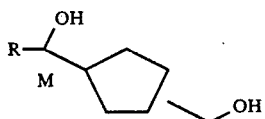
M = Fe, Ni, Co, Mo, Ti, Ru
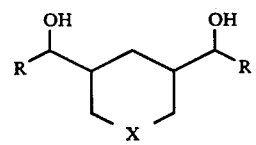
X = CH$_2$, O, S, NH, NR
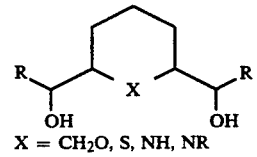
X = CH$_2$O, S, NH, NR
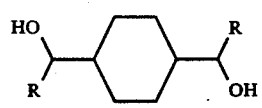
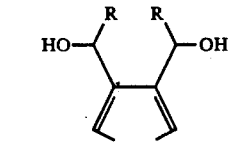
X = CH$_2$, O, S, NH -continued

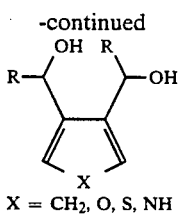

X = CH₂, O, S, NH

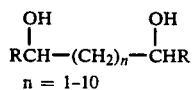

n = 1-10

R = CH₃, CH₂CH₃, CH₂Cl in all cases

Still another preferred group of compounds are those where n is 3 and the compound is selected from the group consisting of the (R,R,R), (R,R,S), (R,S,S), and (S,S,S) stereoisomers thereof.

Typical chemical structures for symmetric, secondary triol monomers are the following.

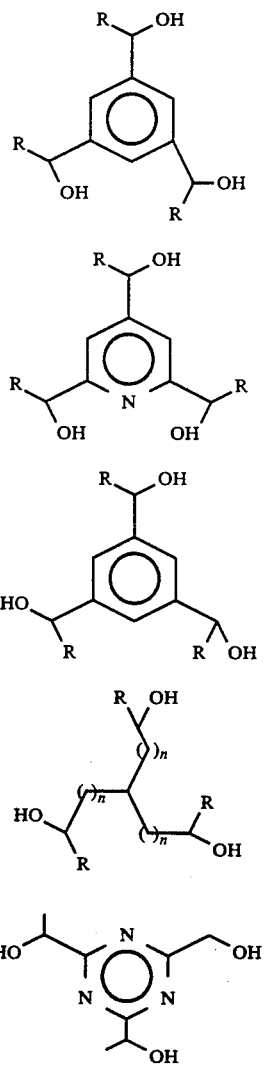

-continued

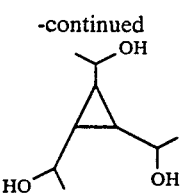

These compounds may be prepared by the methods of the invention or by any other available methods. The present methods, however, permit the large-scale high stereochemical purity preparation of these compounds.

The symmetric, secondary diol and triol monomers of stereochemical purity of this invention are suitable for the preparation of polymers with non-linear optical properties. Examples of such polymers are helical polymers of single screw sense for they are unable to crystallize into a centrosymmetric crystal. By means of example, a computer model of a polymer built from the diols utilized in the examples showed a perfect helix for their polycarbonate structures. The pitch and period of the helical polymers can be further adjusted by varying the diol or triol stereoisomer utilized. The nitrogen-containing compounds also permit the binding of metals to the helix to make chiral catalysts. The polymers are also of value for chromographic separation of other stereoisomer mixtures.

The polymers of the invention can be any polymers formed by block or alternative binding of the present diol and triol stereoisomers with other bridging structures. By means of example, the polymers of the invention may have the general formula

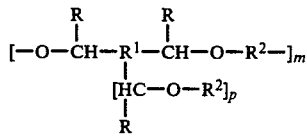

wherein

R and $R^1$ are different from one another and are selected from the group consisting of $(C_1-C_{20})$alkyl, alkenyl or alkynyl, $(C_3-C_{22})$cycloalkyl and $(C_4-C_{22})$aryl, said alkyl, alkenyl, alkynyl, cycloalkyl and aryl may be substituted with N, O or S in the ring or chain structure, and said alkyl, alkenyl, alkynyl, cycloalkyl and aryl may be further substituted with $(C_1-C_4)$alkyl, alkenyl or alkynyl, halogen, $(C_2-C_{10})$alkoxy or aryloxy, $NO_2$ or $NHCOR^4$, wherein $R^4$ is H, $(C_1-C_6)$alkyl, alkenyl or alkynyl, or $(C_4-C_{10})$aryl which may be further substituted with N, S or O; and $R^2$ selected from the group consisting of —CO— —CO—$R^3$—CO,$(CH_2)_q$, 1,2-, 1,3-, 1,4-$(C_6H_4)$, biphenylene and —CONH—$R^3$—NHCO, wherein $R^3$ is $(C_1-C_{10})$alkyl, alkenyl or alkynyl or $(C_4-C_{20})$aryl, alkylaryl or cycloalkyl or

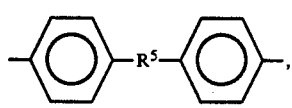

wherein $R^5$ is $(C_1-C_{10})$alkyl, alkenyl or alkynyl, $(C_3-C_{20})$cycloalkyl or $(C_4-C_{14})$ aryl, all of which may be further substituted with N, S or O in the ring or chain structure, and/or with halogen, $NO_2$ or $(C_1-C_4)$-alkoxy; alkoxy;

q is 1 to 12;

m is 1 to 10,000; and p is 0 to m.

In a particularly preferred embodiment the polymer comprises a lesser amount of triol (about 0.001 to 20 wt %) plus diol and bridging units, $R^2$ (about 80 to 99.99wt %) to give cross linked polymer. More preferably, the polymer comprises about 0.1 to 10 wt % of triol, the remainder being diol and bridging units, $R^2$.

The polymers of this invention may be prepared by methods known in the art from the stereochemically substantially pure compounds of the invention and reactive compounds which may act as bridges between residues of the diol and/or triol molecules. Examples of such bridging polymers are derivatized polycarbonates, polyesters, polyethers and polyurethanes, among others. For all practical purposes, any known compounds having two groups which can react with alcohols may be utilized along with the present diol compounds in the formation of optically active or stereochemically fixed polymers, The following residues are provided by means of example.

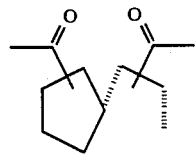

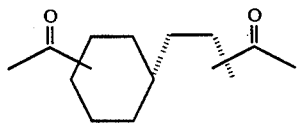

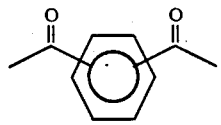

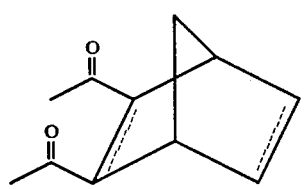

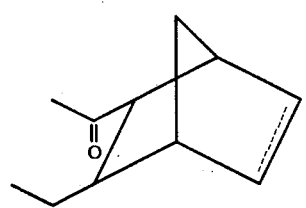

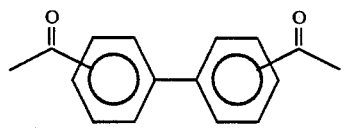

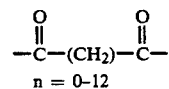

n = 0–12

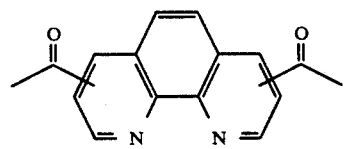

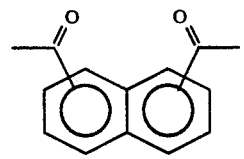

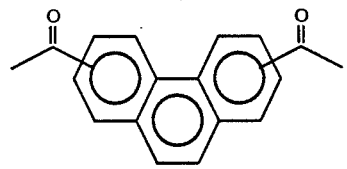

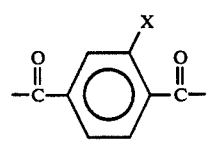

X = Cl, Br, I, $CH_3$ $CH_2CH_3$, $OCH_3$

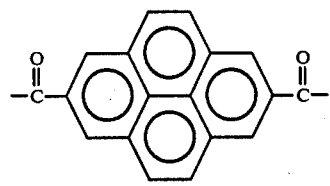

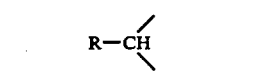

R = H, $CH_3$, $CCl_3$, $C_6H_5$

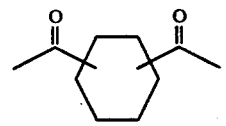

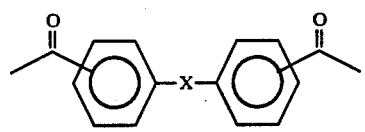

X = O, S, CH=CH, C≡C, $SO_2$

-continued

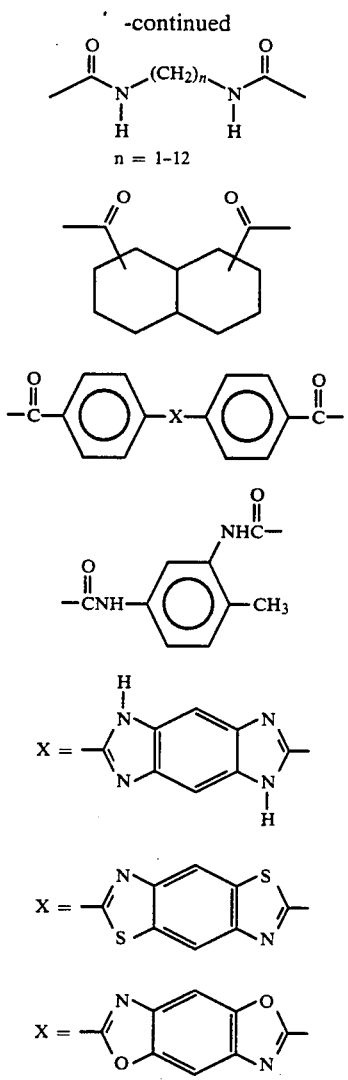

Typical bridging residues are carbonyl, acyl, diacyl, aldehyde, dialdehyde, imide, diimide, urethane, diurethane and the like.

The following are examples of methods for preparing the polymers of this invention, although not a comprehensive list. The polyesters may be prepared by direct esterification (British Patent 604,985 to the Chemstrand Corporation; A. Fradet and E. Morechal, *Advances in Polymer Science*, 43, pg. 51-98 (1982)), transesterification or ester exchange (G. A. Haggis and L. N. Owen, *J. Chem. Soc.*, 1953, 44; C. S. Marvel and J. H. Johnson, *J. M. Chem Soc.*, 72, 1674 (1985)), the reaction of acid halides with diols (K. Yamaguchi, M. Takayanagi, and S. Kuriyama, *J. Chem. Soc.* (Japan), *Ind. Chem. Sec.* 58, 358 (1955); U.S. Pat. No. 2,623,034 to P. J. Flory and F. S. Leutner, (Dec. 23, 1952)) and the reaction of dicarboxylic acid salts with diols (Brit. Patent 590,451 to J. T. Dickson, H. P. W. Huggill and J. C. Welch), among others. A review of methods of preparing polyesters is provided by Pilati (F. Pilati, in *Comprehensive Polymer Science*, Vol. 5, pp 275-315, 1988). The polycarbonates may be prepared by the method of Schnell (Schnell, H, *Ind. and Emg. Chem*, 51:157 (1959), the Bayer methods (Fabriken Bayer A. G., GB Patent Nos. 546,376 and 875,378), and/ or the Frecht et al method (Frecht et al, *Polym. J.* (Tokyo) 19(1):31(1987)). The polyurethanes may be prepared by the method of Alexander et al (Alexander et al, in "Some Aspects of Textile Research in Germany", H. M. Stationary Office, London (1947)), the method of Lyman (Lyman, D. J., *J. Poly. Sci.* 45:49 (1960)) and/or the Wittbecker et a method (Wittbecker et al, *J. Poly. Sci.* 40:367(1959)). The polyethers may be prepared as disclosed in *Polymer Chemistry*, p. 152, Chapman and Hill, London (1973)). However, other methods known in the art may also be utilized.

Also part of this invention is a method of separating the stereoisomers of the compounds of the invention, said method comprising obtaining a stereochemical mixture of a secondary alcohol of the formula $R^1(-HC(-R)(-OH))_n$, wherein n is 2 or 3, and R and $R^1$ are as described above;

reacting the alcohol mixture with a $R^7$ acyl anhydride or a $R^6OCOR^7$ ester, wherein $R^6$ is $(C_1-C_4)$alkyl, $CF_3CH_2$, $CCl_3CH_2CN$, in the presence of an enzyme capable of stereoselectively acylating the (R) site of a secondary alcohol, said alcohol mixture, anhydride and enzyme being provided in a medium, in proportions and under conditions effective to form an (R) (or (S) site(s)) acyl ester(s) of the secondary alcohol; and separating the (S,S) or (S,S,S) (or (R,R) or (R,R,R)) secondary alcohol, the (R,S) or (R,S,S) (or R,R,S)) monoacyl ester of the secondary alcohol, the (R,R) or (R,R,S) (or (S,S) or (R,S,S)) diacylester and/or the (R,R,R) (or (S,S,S)) triacylester of the secondary alcohol stereoisomers from one another and from the reaction medium.

Racemic mixtures of secondary alcohols suitable for use as substrates in this method are either commercially available or may be prepared by methods known in the art. The racemic mixture of the secondary alcohol is reacted with an acyl anhydride or an ester in the presence of an enzyme capable of stereoselectively acylating the (R) (or the (S)) site of a secondary alcohol. The reactants are provided in a liquid organic medium, which is preferably anhydrous or nearly anhydrous, and the reaction may optionally be conducted in a non-oxidizing atmosphere, such as nitrogen gas, and at a temperature of about $-10°$ to $150°$ C., more preferably about $10°$ to $60°$ C., and still more preferably about $20°$ to $40°$ C. The enzyme utilized for this reaction step may be a lipoprotein lipase such as that obtained from Pseudomonas sp, and sold under the trade name "Amano P". However, any enzyme possessing the desired stereoselectivity is suitable.

Suitable organic compounds for use as the medium are "solvents" able to dissolve or at least partially suspend the secondary alcohol, such as benzene, toluene, xylene, ether, tetrahydrofuran, and dichloromethane, but which do not cause the enzyme to lose its activity. The solvent should also not act as a catalyst for esterification of the diol (or triol)).

The acyl anhydride may be a $(C_1-C_{20})$acyl anhydride, although acetic anhydride is preferred because it is easily obtained and inexpensive. Particularly suitable proportions of acyl anhydride alcohol mixture, and enzyme are about 10:1:0.5 to 1:1:0.005 mmol:mmol:g, more preferably 5:1:0.25 to 1:1:0.25 mmol:mmol:g, and still more preferable about 1.5:1:0.025 to 2.5:1:0.075 mmol:mmol:g.

The free alcohol, mono-, di- and/or tri- acyl esters of the alcohols may be separated by applying technology known in the art. Preferred are fractional distillation, chromatography, temperature-controlled precipitation, or combinations of these procedures. By fractional distillation is meant the application of heat to the reaction mixture and the distillation at different temperatures of the various products. Chromatography may be conducted by column chromatography, high pressure liquid chromatography, gel permeation chromotography, gas permeation chromatography and the like, as is known in the art. By temperature-controlled precipitation it is meant the utilization of temperatures, with or without a solvent, which will permit the selective crystallization and/or precipitation of one of the stereoisomers in the presence of the remaining ones. This procedure may be repeated at different temperatures and/or with different solvents for separating the different stereoisomers or it may be combined with any of the other procedures for the further separation of the other stereoisomers.

The conditions for the separation of the stereoisomers in the form of free diol or triol, monoacyl esters, diacyl esters and/or triacylesters can be easily adjusted by a person with skill in the art. Solvents or combinations thereof suitable for the separation of alcohols from esters may be utilized as is known in the art to attain the chromatographic separation or temperature-controlled precipitation of the stereoisomers. The conditions for conducting the fractional distillation and the temperature-controlled precipitation of the stereoisomers are routinely adjusted by a practitioner in the laboratory.

The free diols may be obtained from the acyl ester derivatives by chemical or enzymatic hydrolysis, which methods are known in the art. Thus, after the free diol or triol, the monoacyl ester, the diacyl ester and/or triacylester are separated from one another and from the reaction medium, the acyl esters may be separately hydrolyzed to free their corresponding alcohol stereoisomers.

In a particularly preferred form of practicing the stereoselective acylation method, the enzyme is provided on a solid support and the alcohol mixture and the acyl anhydride are reacted in the presence of the solid supported enzyme. Solid supported enzymes such as those suitable for the practice of this method are commercially available or can be prepared by methods known in the art.

During the separation of the stereoisomers, it is preferable to first separate the enzyme from the reaction medium and then proceed with the separation of the stereoisomers from one another. In this manner, the stereoisomers are obtained with high purity and the enzyme may be recycled for further use.

In order to attain a higher degree of stereochemical purity for any particular stereoisomer with respect to the others, the method of the invention may be repeated using partially purified diol or triol stereoisomer and a more selective acylation of the (R) (or (S)) site of the alcohol, monoacyl ester and/or diacylester of the alcohol attained. This is desirable in cases where only a partial acylation of a site is attained. The conditions for conducting successive acylation reactions are similar to the original ones. The overall conditions may be adapted for attaining the, e.g., further acylation of a second or third (R) (or (S)) site which in general is more difficult to acylate than the first one, and the like.

After completion of the reaction, the stereoisomers can be separated as described above. Each stereoisomer of the free alcohol may thus be obtained substantially free of the other stereoisomers by chemical or enzymatic hydrolysis of the corresponding acyl esters.

Also provided herein is a method of separating the stereoisomers of a stereochemical mixture of secondary alcohols as described above, said method comprises obtaining a stereochemical mixture of the esters of the formula $R^1(-CH(-R)(-OR^2)_n$, wherein n is 2 or 3, and R and $R^1$ are as described above, and $R^2$ is $(C_1-C_{20})$acyl;

reacting the racemic ester with an enzyme capable of selectively deacylating the (R) (or (S)) site of a secondary alcohol, said ester and enzyme being provided in an aqueous or partially aqueous medium in a proportion and under conditions effective to produce (R) (or (S)) site deacylated isomers of the secondary alcohol; and separating the (R,R) or (R,R,R) (or (S,S) or (S,S,S)) free alcohol, the (R,S) or (R,R,S) (or (R,S,S)) monoacyl ester, the (S,S) or (R,S,S) or (R,S,S) (or (R,R) or (R,R,S)) diacylester and the (S,S,S) (or (R,R,R)) triacyl ester stereoisomers of the alcohol from one another and from the reaction medium.

The stereochemical mixture of the acyl esters can be obtained commercially or be prepared in the laboratory by methods known in the art. Typically, the $(C_1-C_6)$ acyl esters are easily prepared in the laboratory by acetylation of stereochemical mixtures of the alcohols as described by Hassner et al, Sonntag and/or Harrison et al (Hassner et al, *Tetrahedron Letters*, 4475 (1978); Sonntag, *Chem. Rev.*, 52:312 (1953); Harrison et al, *Chem. Ind.* (London), 1568 (1968)). However, other methods may also be utilized as are known in the art.

The stereochemical mixture of acyl esters is reacted with an enzyme which stereoselectively deacylates the (R) (or (S)) site of a secondary alcohol such as a lipoprotein lipase, e.g., the lipase from Pseudomonas sp.

Depending on the general chemical structure of a compound, a site recognized by the enzyme may be called (R) or (S). However, it is the same group of enzymes which do recognize both types of sites.

In a preferred embodiment of the method, the enzyme is provided on a support and the supported enzyme is reacted with a racemic acyl ester in an aqueous medium, where the pH is controlled throughout the reaction. Suitably the pH of the reaction may be about 6 to 8, more preferably about 6.5 to 7.6, and still more preferably from about 7 to 7.4. The pH of the aqueous medium may be controlled by a buffer and the addition of base or acid when necessary to maintain a substantially constant pH within about 1 pH unit.

The deacylation reaction is generally conducted at a temperature from about 10° to 50° C., more preferably about 15° to 40° C., and still more preferably about 20° to 30° C. The enzyme is added in a proportion to the acyl ester of about 1:200 to 1:1 g:mmol, and more preferably about 1:25 to 1:15 g:mmol.

The separation of the (R,R) or (R,R,R) (or (S,S) or (S,S,S)) free alcohol, the (R,S) or (R,R,S) (or (R,S,S)) monoacyl ester, the (S,S) or (R,S,S) (or (R,R) or (R,R,S)) diacyl ester and/or the (S,S,S) (or (R,R,R)) triacyl ester (comprising different stereoisomers of the alcohol) from one another and from the reaction medium may be conducted as described previously. Suitable technology for the separation step is fractional distillation, chromatography, temperature-controlled fractional precipitation and combinations of these known techniques.

As in the case of the diols, the separation of the triol stereoisomers may further encompass the separate hydrolysis of the different acyl esters to form the free triols. This hydrolysis may be undertaken by chemical or enzymatic means, all of which are known in the art, as are the conditions for conducting the reactions. The free alcohol stereoisomers may then be separated from the reaction medium by any of a number of known techniques such as temperature-controlled precipitation, chromatography, extraction and the like.

In a particular embodiment of this method, the enzyme, if supported, may be separated from the reaction medium prior to separating the stereoisomers. This may be attained by filtration, centrifugation, and the like, all techniques known in the art.

The separation of the diols or triols may also comprise further reacting the separate fractions comprising the various stereoisomers of the alcohol and acyl esters thereof with further enzyme to selectively deacylate the (R) (or (S)) site(s) of the acyl esters of the alcohol which were not fully deacylated previously as described above. The repetition of this step and the further separation of the deacylated stereoisomers is most useful when the first reaction has not gone to completion. In other words, when there remain unreacted (R) (or (S)) site acyl esters following the initial enzymatic hydrolysis of the stereochemical mixture, repeating the steps more than once using the partially purified stereoisomer fractions increases the purity of the product and its yield.

The present methods are particularly suitable for diols and triols where the two chiral centers are removed from one another by at least about 2 carbon atoms. This permits the reaction catalyzed by the enzyme at each site to proceed in a manner substantially independent from the other site. The method of the invention is generally described hereinbelow as applied to the separation of a racemic mixture of α,α'-dimethyl-1,4-benzenedimethanol. The following Scheme and description shows the general method of this invention as applied to a specific separation.

ondary alcohols, the product mixture includes three components.

Unreacted diol having the (S,S) configuration,
Monoacylated diol having the (R,S) configuration, and
Diacylated diol having the (R,R) configuration.

The mixture is then separated by standard techniques such as distillation or chromatography. In the case of, e.g., the α,α'-dimethyl-1,4-benzendimethanol shown in the examples, the (S,S) diol crystallizes from the mixture upon cooling, and only the (R,S)-monoacetate and (R,R)-diacetate need be separated by chromatography. Following separation, the acylated compounds are hydrolyzed to regenerate the (R,S) and (R,R)diols.

Having now generally described this invention, the same will be better understood by reference to certain specific examples, which are included herein for purposes of illustration only and are not intended to be limiting of the invention or any embodiment thereof, unless so specified.

EXAMPLES

Example 1

Preparation of the Stereoisomer Mixture of α,α'-Dimethyl-1,4-benzenedimethanol (S,S), (R,S), and (R,R) Stereoisomers of Compound 1)

A 250 mL three-necked round bottom flask fitted with a magnetic stirrer and a nitrogen inlet was charged with 10.0 g (61.7 mmol) of 1,4-diacetylbenzene (Aldrich) and 120 mL of anhydrous isopropyl alcohol. To the stirred solution were added 2.3 g (60.8 mmol) of sodium borohydride in three equal portions. The mixture was heated to reflux and the reaction monitored by thin layer chromatography (TLC). After 2 hours, the starting material had been consumed and a single new spot remained.

Scheme

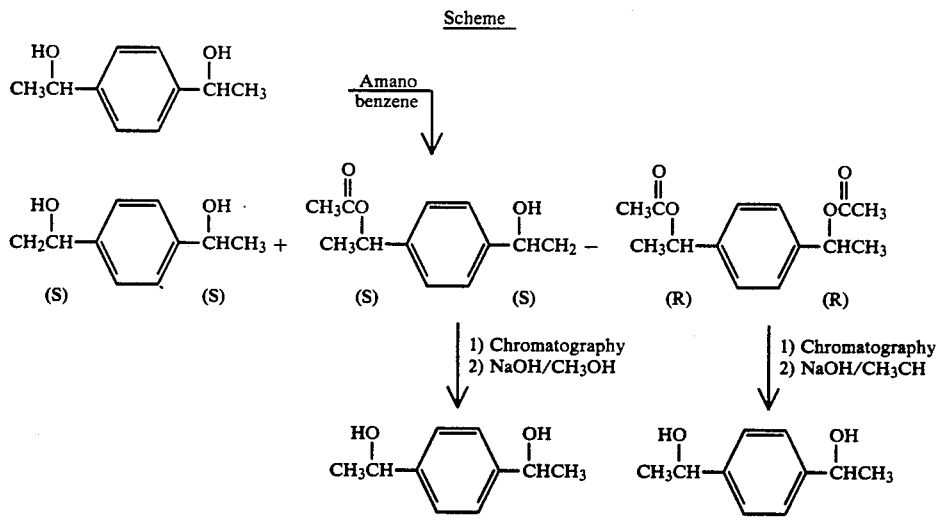

The diol mixture is dissolved or suspended in an anhydrous organic solvent under a non-oxidizing atmosphere, such as $N_2$ gas. The enzyme catalyst is added, followed immediately by, e.g., two equivalents of acetic anhydride. The progress of the reaction is followed, e.g., by VPC. When the reaction is completed, as indicated by a dramatic reduction in its rate, it is stopped by filtering out the enzyme. Based on the known selectivity of the lipase enzyme for catalyzing the esterification of chiral centers having the (R) configuration of sec- The reaction was quenched by addition of 50 mL of water. After stirring to destroy excess sodium borohydride, the solvents were evaporated and the residue was extracted with 3×100 mL ethyl acetate. The combined organic extracts were washed with 2×100 mL of water, dried over sodium sulfate and the solvent evaporated to yield 9.1 g of diol mixture.

M.P.(Melting Point): 82°-83° C. (Lit. Value: 80°-81° C., Mowry et al., *J. Am. Chem. Soc.* 1946, 68, 1105).

IR (KBr): 3350, 2950, 1515, 1440, 1360, 1295, 1210, 1080, 1005, 900, 830 cm$^{-1}$.

$^1$H NMR (CDCl$_3$): δ 7.33 (s, 4 H), 5.87 (q, 2 H), 2.27 (s, 2 H), 1.51 (d, 6 H).

Example 2

Separation of the Stereoisomers of α,α'-Dimethyl-1,4-benzenedimethanol

A 500 mL three-necked round bottom flask equipped with a magnetic stirrer and a nitrogen inlet was charged with 6.98 g (42.0 mmol) of the stereoisomer mixture of 1 and 250 mL of anhydrous benzene. The mixture was heated to obtain a clear solution, then cooled to ambient temperature, and 4.4 g of Amano P lipoprotein lipase (AMANO Int'l Enzyme Co., Troy, Va.) was added with stirring followed by 8.57 g (84.0 mmol) of acetic anhydride.

After 6 hours a marked change in the rate of disappearance of Compound 1 and appearance of products was observed by vapor phase chromatography (VPC), and after 7 hours the reaction was quenched by filtering off the catalyst.

Example 3

Isolation of
(S,S)-α,α'-Dimethyl-1,4-benzenedimethanol
(Compound (S,S) 1)

Approximately half of the solvent was evaporated and the concentrated mixture stored at 0° C. overnight. The frozen benzene was allowed to thaw and the colorless crystals of the compound (S,S) 1 which remained were filtered off. The product obtained had the following characteristics.

1.68 g, 24.1% of the starting material.

MP: 128°-130° C. (after recrystallization from benzene).

The $^1$H and $^{13}$C NMR spectra were identical with those described above for the stereoisomer mixture.

[α]$_D^{25}$ −79.9°. (c=2, acetone).

Example 4

Isolation of
(R,S)-α,α'-Dimethyl-1,4-benzenedimethanol
Monoacetate (Compound (R,S) 2)

The filtrate from isolation of the (S,S) 1 compound was washed with 2×50 mL of aqueous potassium carbonate and 50 mL of water, then dried over sodium sulfate, and the solvent evaporated at ambient temperature.

The residual yellow oil was purified by flash chromatography on a 6 inch bed of Merck 60/60 Angstrom silica gel and eluted with 1:1 hexane/ethyl acetate to give two fractions. The second fraction, comprising 3.54 g of a colorless oil, was shown to be the (R,S) 2 compound and accounted for 40.1% of the starting diol mixture.

[α]$_D^{25}$: +59.3°. (c=4, acetone).

$^1$H NMR (CDCl$_3$): δ 7.35 (S, 4 H), 5.84 (q, J=6.6 Hz, 1H), 4.83 (q, J=6.5 Hz, 1H), 2.68 (br s, 1H), 2.03 (S, 3 H), 1.51 (D, J=6.6 Hz, 3 H), 1.45 (D, J=6.5 Hz, 3 H).

$^{13}$C NMR (CDCl$_3$): δ 170.3, 145.4, 140.5, 126.0, 125.4, 72.0, 69.7, 24.9, 21.9, 21.1.

Example 5

Isolation of (R,R)
-α,α'-Dimethyl-1,4-benzenedimethanol Diacetate
(compound(R,R)-3)

The first fraction comprising 2.56 g of a colorless oil was shown to be the (R,R) isomer of compound 3 and accounted for 24.4% of the starting diol mixture.

[α]$_D^{25}$:+152.9° (c=2, acetone).

$^1$H NMR (CDCl$_3$): δ 7.33 (s, 4 H), 5.87 (q, J=6.6 Hz, 2 H),2.06 (s, 6 H), 1.52 (D,J=6.6 Hz, 6 H).

$^{13}$CNMR(CDCl$_3$): δ$_c$ 170.1, 141.1, 126.1, 71.8, 21.9, 21.1.

Example 6

Isolation of
(R,S)-α,α'-Dimethyl-1,4-benzenedimethanol
(Compound (R,S) 1)

To a solution of 0.396 g (9.90 mmol) of sodium hydroxide and 50 mL of absolute methanol prepared under a dry nitrogen atmosphere were added 2.00 g of the monoacetate (Compound (R,S) 2) in 25 mL of anhydrous methanol.

The mixture was stirred for 2,5 hours after which time VPC analysis showed the hydrolysis to be complete. The solvent was evaporated, 100 mL of water added to the residue, and the mixture stirred rapidly.

The crystalline precipitate which formed was filtered off and dried in vacuo at ambient temperature for 12 hours. It was then recrystallized from hot benzene to give 1.41 g (88%) of the (R,S) 1 compound having the following characteristics.

M.P.: 116°-118° C. (Lit. Value: 90°-91° C. or 114°-115° C., Mowry, D. T. et al. *J. Am. Chem. Soc.*, 1946, 68, 1105). [α]$_D^{25}$: −0.35° (C=2, acetone).

The $^1$H and $^{13}$C NMR spectra was identical with those described above for the stereoisomer mixture of compound 1.

Example 7

(R,R)-α,α'-Dimethyl-1,4-benzenedimethanol
(Compound (R,R) 1)

In a manner analogous to that described for the monoacetate, 1.50 g (6.0 mmol) of the diacetate, (Compound (R,R) 3), were treated with 0.48 g (12.0 mmol) of sodium hydroxide to provide 0.91 g (92%) of compound (R,R) 1 as colorless needles. The product had the following characteristics.

M.P.: 130°-131.5° C. (Lit. Value: 92°-94° C., Holland et al, *Can. J. Chem.*, 1987, 65, 502, or 90°-91° C., 114°-115° C., Mowry, et al. *J. Am. Chem. Soc.*, 1946, 68, 1105).

[α]$_D^{25}$: +80.5° (c=2, acetone), +74.8° (c=2, ethanol), (Lit. +60° C. not given, ethanol or chloroform: Mowry, D. T., Renoll, M., Huber, W. F., *J. Am. Chem. Soc.*, 1946, 68, 1105).

The $^1$H and $^{13}$C NMR were identical with those described above for the stereoisomer mixture of compound 1.

Example 8

Stereochemical Purity of the (R,R) and (S,S) Stereoisomers of α,α'-dimethyl-1,4-benzenedimethanol No direct measure for the optical purities of the (R,R) and (S,S)-α,α-dimethyl-1,4-benzenedimethanol utilized in the present examples has been found in the literature.

The compounds prepared by the method described here have significantly higher values for $[\alpha]_D^{25}$ −79.9° and +80.5° (c=2, acetone) or +74.8 (c=2, ethanol) than the value of +60° (c not reported, ethanol?) previously reported for the (R,R)-diol formed by enzymatic oxidation of p-diethylbenzene (Holland, H. L.; Bergen, E. J.; Chenchaiah, C.; Khan, S. H.; Munoz, B.; Ninniss, R. W.; Richards, D, Can. J. Chem., 1987, 65, 502). An enatiomeric excess of >97% was purported for this product on the basis of its behavior in the presence of a chiral NMR shift reagent suggesting this is not a valid method for determining the stereochemical purity of these diols.

The two enantiomers prepared in the present study, on the contrary, are optically pure. Their rotations differ by only 0.75% in magnitude. The (S,S)-enantiomer contains minor amounts of impurities while the rotation of the meso compound is essentially zero.

Since the enzyme must select the (R,R)-stereoisomer twice and the (R,S)-stereoisomer once and must always reject the (S,S)-stereoisomer, impure compounds having this set of specific rotations would not occur fortuitously.

Example 9

Separation of α,α'-dimethyl-1,3-benzenedimethanol stereoisomers

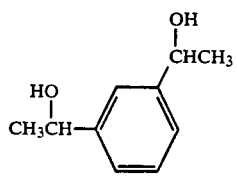

The acylation was significantly slower using this substrate, apparently because of steric factors, or because the enzyme is inhibited by the unreactive stereoisomers.

When the reaction was stopped after 22.5 hrs, not all (R) chiral centers had reacted. Rather, it appears that acetylation of the (R) chiral center in the (R,S) or meso stereoisomer and one of the chiral centers in the (R,R) stereoisomer occurs rapidly, but the second chiral center of the (R,R) stereoisomer reacts more slowly.

As a result, the meso diol monoacetate fraction was contaminated with (R,R) diol monoacetate. Hydrolysis of the monoacetate fraction, therefore, led to diol having $[\alpha]_D^{25}$ +7.68° rather than the expected 0.0°. The unchanged (S,S) diol and the diacetylated (R,R) diol appear to be enantiomerically pure.

Based on the $[\alpha]_D^{25}$ +65.9°, found for the (R,R) stereoisomer, after hydrolysis of the diacetate, the (R,S) diol fraction contains an 11.6% impurity of (R,R) material.

When the (R,S) diol fraction was again subjected to the enzymatic separation procedure, the reaction proceeded much more rapidly, and, when complete, was shown by VPC analysis to contain precisely 11.6% of diacetate. This observation supports the value used as the specific rotation of the pure (R,R) enantiomer being correct. The recycling process provided meso diol containing an impurity of only 1.1% of (R,R) diol.

The conditions for the reaction were as described in Examples 10 to 17 below.

Example 10

Preparation of the Stereoisomer Mixture of α,α'-Dimethyl-1,3-benzenedimethanol (Compounds (S,S), (R,S), and (R,R) 4)

This mixture of stereoisomers was prepared from 1,3-diacetylbenzene by reduction with sodium borohydride as described above for the para stereoisomers. The mixture of stereoisomers was isolated as a semisolid. It appeared as a single spot on TLC and as a single peak on VPC.

$^1$HNMR(CDCl$_3$): δ 7.2–7.4 (m, 4 H), 4.85 (q, 2 H), 2.95 (br s, 2 H), 1.46 (d,6 H).

$^{13}$CNMR(CDCl$_3$): δ 146.0, 128.4, 124.8, 123.0, 69.9, 25.0.

Example 11

Separation of the Stereoisomers of α,α'-Dimethyl-1,3-benzenedimethanol.

A benzene solution containing 10.1 g of the mixture of stereoisomeric diols (Compound 4) was treated with Amano P enzyme and acetic anhydride as described above for the para diols, 1. The reaction was allowed to continue for 22.5 hours then the products were separated as before.

Example 12

Isolation of (S,S)-α,α'-Dimethyl-1,3-benzenedimethanol (Compound (S,S) 4)

The insoluble (S,S)-diol, 1.65 g, corresponding to 16.3% of the starting mixture of diols, was filtered off. It displayed the following characteristics.

$[\alpha]_D^{25}$: −63.6° (C=2, acetone).

The $^1$H and $^{13}$C NMR spectra were identical with those described above for the stereoisomer mixture.

Example 13

Isolation of (R,S)-α,α'-Dimethyl-1,3-Benzenedimethanol Monoacetate (Compound (R,S) 4).

6.65 g of the monoacetate of compound (R,S) 4, corresponding to 52.5% of the starting mixture of diol stereoisomers were isolated by chromatography as described above for the para isomer. The monoacetate of the (R,S) compound displayed the following characteristics.

$[\alpha]_D^{25}$: +53.1° (c=2.2, acetone).

$^1$HNMR(CDCl$_3$): 7.2–7.4(m, 4 H), 5.85 (q, J=6.6 Hz, 1 H), 4.85 (q, J=6.5 Hz, 1 H), 2.55 (br s, 1 H), 2.04 (s, 3 H), 1.52 (d, J=6.6 Hz, 3 H), 1.47 (d, J=6.5 Hz, 3 H).

$^{13}$CNMR(CDCl$_3$): δ$_c$ 170.3, 146.0, 141.6, 128.4, 124.9, 124.8, 123.0, 72.2, 69.9, 25.0, 22.0, 21.1.

Example 14

Isolation of (R,R)-α,α'-Dimethyl-1,3-benzenedimethanol Diacetate 2.77 g of the diacetate of the (R,R) isomer of compound 4 corresponding to 18.2% of the starting mixture of diol stereoisomers, were isolated by chromatography as described above for the para isomer. The (R,R) diacetate of Compound 4 displayed the following characteristics.

$[\alpha]_D^{25}$: +111.3° (c=2, acetone).

$^1$HNMR(CDCl$_3$): δ 7.2–7.4 (m 4 H), 5.85 (q, J=6.6 Hz, 2 H), 2.04 (s, 6 H), 1.52 (d, J=6.6 Hz, 6 H).

13CNMR(CDCl3): $\delta_c$ 170.3, 141.6, 128.4, 124.9, 123.0, 72.2, 22.0, 21.1.

Example 15

(R,S)-α,α'-Dimethyl-1,3-benzenedimethanol Compound (R,S) 4)

The monoacetate of the (R,S) 4 compound was hydrolyzed with sodium hydroxide in absolute methanol as described for the para compound above. To prevent re-acetylation of the alcohols, it was necessary to neutralize the reaction mixture to pH 6.5 with methanolic HCl before evaporation of the methanol. It displayed the following characteristics.

$[\alpha]_D^{25}$: +7.68° (c=2, acetone).

The 1H NMR spectrum was identical with that of the mixture of the diol stereoisomers.

The rotation of +7.68° indicates this meso compound is contaminated with 11.6% of the compound (R,R)-(+) 4 having a rotation of +65.9°.

Example 16

(R,R)-α,α'-Dimethyl-1,3-benzenedimethanol (Compound (R,R) 4).

0.42 g of the diacetate of the compound (R,R) 4, (1.68 mmol), were hydrolyzed with 0.132 g, (3.3 mmol); of sodium hydroxide in 50 ml of anhydrous methanol as described for compound (R,R) 3 above. To prevent reacetylation of the hydrolyzed diol it was necessary to adjust the mixture to pH 6.5 with methanolic HCl before evaporating the methanol.

Following the extraction of the diol into methylene chloride and evaporation of the solvent, 0.25 g (90%) of compound (R,R) 4 were recovered. This compound displayed the following characteristics.

$[\alpha]_D^{25}$: +65.9° (C=2, acetone).

The 1H NMR spectrum was identical with that of the mixture of diol stereoisomers.

Example 17

Purification of the (R,S)-α,α'-Dimethyl-1,3-benzenedimethanol by Recycling

A 4.32 g sample of the impure (R,S)-α,α'-dimethyl-1,3-benzenedimethanol isolated above was subjected to a PPL enzyme catalyzed acetylation by acetic anhydride as described above. In the absence of any (S,S) diol, the reaction was completed after 11 hours. VPC analysis showed the presence of 11.6 wt % of diacetate along with the monoacetate.

Separation of the mixture by chromatography gave 2.61 g of the monoacetate of the compound (R,S)-4 corresponding to a recovery of 2.08 g of the diol (compound (R,S) 4). The monoacetate displayed the following characteristics.

$[\alpha]_D^{20}$: +57.6° (C=2, acetone).

A second fraction contained 0.81 g of the diacetate of compound (R,R) 4, corresponding to 0.54 g of the (R,R)-diol, which displayed the following characteristics.

$[\alpha]_D^{20}$: +110.8° (C=2, acetone).

Hydrolysis of the monoacetate as described previously gave the meso diol (compound (R,S) 2), having a $[\alpha]_D^{20}$: +0.77° (C=2, acetone) indicating an impurity of 1.1% of Compound (R,R) 4.

Example 18

Separation of α,α'-dimethyl-4,4'-biphenyl dimethanol

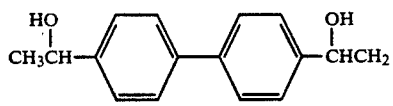

This substrate has very low solubility in benzene. After eight hours, the reaction stopped despite the fact that acetylation would be expected to maintain an equilibrium concentration of the (R,R) and (R,S) diols.

Filtering off the catalyst and undissolved diol followed by evaporation of the benzene provided the expected mixture of diol, monoacetate and diacetate. The (S,S)-diol was contaminated with (R,R) and (R,S) diol as expected. The total weight of product was approximately one third that expected.

The catalyst and unreacted diol were again suspended in benzene and the process described above repeated. A third repetition completed consumption of the diol molecules having (R) chiral centers.

The unchanged diol fractions from the three reactions were combined and again treated with acetic anhydride in the presence of the enzyme. After filtering off the enzyme the benzene was cooled and the (S,S)-diol precipitated. Its rotation $[\alpha]_D^{25} = -76°$, compares favorably with $[\alpha]_D^{25} = +77°$ found for the (R,R) stereoisomer, after hydrolysis of the diacetate.

Example 19

Preparation of the Stereoisomer Mixture α,α'-Dimethyl-4,4'-biphenylenedimethanol Compounds (S,S)-, (R,S)-, and (R,R)-6

This mixture of stereoisomers was prepared from 4,4'-diacetylbiphenyl by reduction with sodium borohydride described above for the para stereoisomers, 1. The mixture of stereoisomers was isolated a solid and appeared as a single spot on TLC.

mp 160°–163°.

1HNMR(CDCl3): delta 7.35–7.70 (AA'BB' quartet, 8 H) 4.95 (crude q, 2 H) 1.89 (d, 2 H), 1.53 (d, 6 H).

Anal. Calcd for $C_{16}H_{18}O_2$: C, 79.24; H, 7.49.

Found: C, 79.11; H, 7.43.

Example 20

Separation of the Stereoisomers of α,60'-Dimethyl-4,4'-biphenylenedimethanol

A mixture containing 4.0 g (16.5 mmol) of the mixture of stereoisomeric diols 6, 3.37 g (33.05 mmol) of acetic anhydride and 2.52 of Amano P lipase supported on Celite 577 in 1250 mL of dry benzene was allowed to stir for 10 hrs. The reaction was stopped by filtering off the catalyst. Evaporation the solvent provided only 1.62 g of product, so the solid which had been filtered off was resuspended in 150 mL of dry benzene and treated with a further 3.0 g (29.4 mmol) of acetic anhydride, this time for a period of 30 hrs. Work up as before provided an additional 1.54 g of product.

A third repetition of the acetylation provided a final 1.38 g of product. The combined products (4.54 g, 97% of theory) were separated by flash chromatography on a 6 in bed of Merck 60/60 A silica gel eluting with 1:1.5 hexane/ethyl/acetate to give, after evaporation of the solvent, three fractions all of which crystallized upon standing.

Example 21

Isolation of (R,R)-α,α-biphenylenedimethanol Diacetate

The first fraction was shown to be the diacetate of compound (R,R)-6: 1.57 g, corresponding to 29.1% of the starting mixture of diol stereoisomers.

M.P.: 77°–80°.

$[\alpha]_D^{25}$: +170.19° (c=2, acetone).

$^1$HNMR(CDCl$_3$): delta 7.50 (AA'BB'q 8 H) 5.92 (q,I=6.6 Hz, 2 H), 2.08 (s, 6 H), 1.57 (d,J=6.6 Hz, 6 H).

Anal. Calcd. for C$_{20}$H$_{22}$O$_4$: C, 73.60; H, 6.79.
Found: C, 73.88; H, 6.82.

Example 22

Isolation of (R,S-α,α-Dimethyl-4,4'-biphenylenedimethanol Monoacetate

A second fraction was shown to be the monoacetate of compound (R,S)-6 : 1.69 g were obtained corresponding to 36.0% of the starting mixture of diol stereoisomers.

M.P.: 70°–72° C.

$[\alpha]_D^{25}$: +62.51] (c=2.2 acetone).

$^1$HNMR(CDCl$_3$): delta 7.5(AA'BB' m, 8 H), 5.92 (q,j =6.6 Hz, 1 H), 4.94 (q,j=6.4 Hz, 1 H), 2.08 (s, 3 H), 1.98 (br s, 1 H), 1.57 (d,j=6.6 Hz, 3 H), 1.53 (d,j −6.4 Hz, 3 H).

Anal. Calcd for C$_{18}$H$_{20}$O$_3$: C, 76.03; H, 7.09.
Found: C, 76.02; H, 7.09.

Example 23

Isolation of (S,S)-α,α-Dimethyl-4,4'-biphenylenedimethanol (S,S-6))

The third fraction was shown to be compound (S,S)-6. 1.10 g were obtained corresponding to 27.5% of the starting mixture of diol stereoisomers. II

M.P.: 158°–160° C.

$[\alpha]_D^{25}$: −55.00° (c=2).

Comparison with the M.P.: and rotation found for the (R,R) isomer suggested contamination by the (R,S) isomer and/or the (R,R) isomer.

Example 24

Purification of (S,S)-α,α'-Dimethyl-4,4'-biphenylenedimethanol (Compound (S,S)-6 by recycling)

The impure (S,S)-6 compound was treated with 0.93 g (9.1 mmol) of acetic anhydride and 0.66 g of the supported Amano P lipase in 100 mL of dry benzene. After 30 hours, the catalyst was removed and, upon cooling the reaction benzene solution to 0° C. the (S,S)-diol (0.91 g, 83%) crystallized as a white solid.

M.P.: 167°–169° C.

$[\alpha]_D^{25}$: −76.05° (c=2, acetone).

The $^1$H and $^{13}$C NMR spectra were identical with those described above for the stereoisomer mixture.

Anal. Calcd. for C$_{16}$H$_{18}$O$_2$: C, 79.24; H, 7.49.
Found: C, 79.28; H, 7.46.

Example 25

(R,S)-α,α'-Dimethyl-4,4'-biphenylenedimethanol

The monoacetate of compound (R,S)-6 was hydrolyzed by treatment with sodium hydroxide in absolute methanol as described for (R,S)-2 above to give 1.31 g (91%) of compound (R,S)-6.

M.P.: 168°–171° C.

$[\alpha]_D^{25}$: +1.45° (c=2, acetone).

The $^1$H NMR spectrum was identical with that of the mixture of diol stereoisomers.

The rotation of +/.45° indicates this meso compound is contaminated with 1.9% of (R,R)-(+)-6 having rotation +76.95°.

Anal. Calcd for C$_{16}$H$_{18}$O$_2$: C, 79.24; H, 7.45.
Found: C,79.07; H, 7.36.

Example 26

(R,R)-α,α'-Dimethyl-4,4'-biphenylenedimethanol (Compound (R,R)-6)

0.42 g of the diacetate of compound (R,R)-6 (1.68 mmol) were hydrolyzed with sodium hydroxide, 0.132 g (3.3 mmol) in anhydrous methanol (50 mL as described for compound (R,R)-3 above to give 1.02 g (88%) of compound (R,R)-6.

M.P.: 168°–170° C.

$[\alpha]_D^{25}$: +76.95° (c=2, acetone).

The $^1$H NMR spectrum was identical with that of the mixture of diol stereoisomers.

Anal. Calcd for C$_{16}$H$_{18}$O$_2$: C, 79.24; H, 7.49.
Found: C, 78.97; H, 7.34.

Example 27

Separation of α,α'-dimethyl 2,6-pyridine dimethanol Stereoisomers

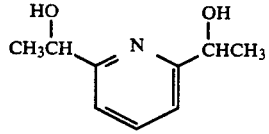

Complete acylation was even slower using this substrate than with the corresponding meta benzenediethanol, possibly because of the added effect of hydrogen bonding between unesterified alcohols and the pyridine nitrogen.

As with the benzene case (compound 4), it appears that acetylation of the (R) chiral center in the (R,S) or meso stereoisomer and one of the chiral centers in the (R,R) stereoisomer occurs rapidly, but the second chiral center of the (R,R) stereoisomer reacts more slowly. The reaction was still incomplete after 47 hours.

To develop evidence that the nitrogen is indeed inhibited, the ability of the pyridinediethanol to catalyze the acylation in the absence of the enzyme was explored. The anhydride was consumed at a rate of 0.4% per hour under these conditions. Only monoacetate was formed in the uncatalyzed process.

Based on the $[\alpha]_D^{25}$ of +10.2°, found for the (R,S) stereoisomer, after hydrolysis of the monoacetate, this fraction contains a significant impurity of (R,R) material.

No attempt has yet been made to recycle the (R,S) stereoisomer and remove the (R,R) impurity, but our success in solving the comparable problem in the benzene and biphenylene system suggests this should be possible. The conditions for the reaction were as described below. The characteristics of the above obtained diols are shown in Table 1 below.

M.P.: 49°–58° C.

$^1$HNMR(CDCl$_3$): delta 7.71 (t, 1 H); 7.21 (d, 2 H); 4.84–4.98 (m. 2 H); 3.91 (s, 2 H); 1.52 (d, 6 H).

Anal. Calcd. for C$_9$H$_{13}$NO$_2$: C, 64.65; H, 7.84; N, 8.38.

Found: C, 64.95; H, 7.60; N, 8.84.

| Remote Diol Stereoisomers Separated by Amano P Catalyzed Stereoselective Acetylation | | | | | | |
|---|---|---|---|---|---|---|
| | R,R | | R,S | | S,S | |
| Diol | Yield$^a$ (%) | Specific$^b$ Rotation | Yield$^a$ (%) | Specific$^b$ Rotation | Yield$^a$ (%) | Specific$^b$ Rotation |
| HO–CH(CH$_3$)–C$_6$H$_4$–CH(CH$_3$)–OH | 22.4 | +80.5° | 35.3 | −0.35° | 24.1 | −79.9° |
| HO–CH(CH$_3$)–C$_6$H$_4$–CH(CH$_3$)–OH (meta) | 16.4 | +65.9° | 41.5$^c$ | +0.77° | 16.3 | −63.6° |
| HO–CH(CH$_3$)–C$_6$H$_4$–C$_6$H$_4$–CH(CH$_3$)–OH (biphenyl) | 25.0 | +76.95° | 32.5 | +1.45° | 22.5 | −76.05°$^d$ |
| HO–CH(CH$_3$)–(pyridine-2,6)–CH(CH$_3$)–OH | 14.9 | +44.01° | 46.5 | +10.21°$^e$ | 14.1 | −42.30° |

$^a$The yield of each component is calculated relative to the total amount of the diol mixture used in the reaction. A statistical mixture would contain 25% (R,R), 25% (S,S), and 50% (R,S) isomer.
$^b$[α]$_D^{amb}$ (c = 2, acetone)
$^c$After recycling through the esterification to remove an 11.6% impurity of (R,R)-diol
$^d$After recycling to remove an impurity of the (R,S)-stereoisomer
$^e$Not recycled to remove the (R,R)-diol impurity

Example 28

Preparation of the Stereoisomer Mixture of α,α-Dimethyl-2,6-pyridinedimethanol (Compounds (S,S)-, (R,S)-, and (R,R)-5)

A 250 mL three-necked round bottom flask fitted with magnetic stirrer and nitrogen inlet was charged with 5.0 g (30.6 mmol) of 2,6-diacetylpyridine and 60 mL of anhydrous isopropyl alcohol. To the stirred solution was added 1.16 g (3.06 mmol) of sodium borohydride in three equal portions. The initially colorless solution became yellow and warmed then slowly returned to pale yellow.

After 1 hr, VPC analysis showed all of the starting material to have been consumed, and, after an additional hour the excess borohydride was destroyed by adjusting the pH to 6.5 with 5% aqueous HCl, about 50 mL being required. After stirring for a short time, the pH was readjusted to 8 with dilute aqueous NaOH solution.

The precipitate which formed was filtered off and the isopropyl alcohol and some of the water evaporated until a volume of about 40 mL was reached. The concentrated aqueous mixture was extracted with 3×100 mL of ethyl acetate.

The combined organic phases were dried over sodium sulfate and the ethyl acetate was evaporated to give 4.20 g (82%) of a nearly colorless oil which crystallized upon standing at 0° C.

Example 29

Separation of the Stereoisomers of α,α'-Dimethyl-2,6-pyridinedimethanol

A 500 mL flask equipped with a magnetic stirrer and a nitrogen inlet was charged with 3.93 g (23.5 mmol) of the stereoisomer mixture of 5 and 150 mL of dry benzene. To the clear, stirred solution was added 2.5 g of Amano P lipase supported on Celite 577 followed by 4.79 g (47.0 mmol) of acetic anhydride.

The reaction was stopped after 45 hrs. by addition of 2 mL of methanol, despite the fact the VPC analysis showed that less than the expected amount of diacetate had been formed. The catalyst was removed by filtration and the filtrate concentrated to yield 4.53 g of a light yellow oil which was separated by flash chromatography on 6 in a bed of Merck 60/60 Angstrom silica gel eluted with 1:1 hexane/ethyl acetate.

Example 30

Isolation of (R,R)-α,α'-Dimethyl-2,6-pyridinedimethanol Diacetate

The first fraction comprising 1.034 g of a pale yellow oil and accounting for 17.5% of the starting diol stereoisomer mixture was shown to be the diacetate of compound (R,R)-5.

[α]$_D^{amb}$: +73.33° (c=2, acetone).

Anal. Calcd. for $C_{15}H_{21}NO_4$: C, 64.50; H, 7.58; N, 5.01.
Found: C, 64.58; H, 7.65; N 5.08.

Example 31

Isolation of
(R,S)-α,α'-Dimethyl-2,6-pyridinedimethanol
Monoacetate

The second fraction, comprising 2.57 g of a pale yellow oil and accounting for 52.5% of the starting mixture of diol stereoisomers, was shown to be the monoacetate of compound (R,S)-5.

$[\alpha]_D^{amb}$: +29.43° (c=2.2 acetone).

Anal. Calcd for $C_{11}H_{15}NO_3$:C, 63.14; H, 7.23; N, 6.70.
Found: C, 63.01; H, 7.30; N, 6.74.

Example 32

Isolation of
(S,S)-α,α'-Dimethyl-2-6-pyridinedimethanol
(Compound (S,S)-5)

The third fraction comprising 0.56 g of a white microcrystalline solid and accounting for 14.2% of the starting mixture of diol stereoisomers was shown to be compound (S,S)-5.

M.P.: 61°-63° C.
$[\alpha]_D^{amb}$: −63.6° (c=2, acetone).

The $^1$H spectrum was identical with that described above for the stereoisomer mixture.

Anal. Calcd for $C_9H_{13}NO_2$: C, 64.65; H, 7.84; N, 8.38.
Found: C, 64.89; H, 7.90; N, 8.45.

Example 33

(R,S)-α,α'-Dimethyl-2,6-pyridinedimethanol
(Compound (R,S)-5

The monoacetate of compound (R,S)-5 was hydrolyzed by treatment with sodium hydroxide in absolute methanol as described for the meta diol (R,S)-4 above. To prevent acetylation of the alcohols it was necessary to neutralize the reaction mixture to pH 6.5 with methanolic HCl before evaporation of the methanol.

Compound (R,S)-5 was isolated as a white semi-solid, 1.42 g (89%).

$[\alpha]_D^{amb}$: +10.21° (c=2, acetone).

$^1$H NMR spectrum was identical with that of the mixture of diol stereoisomers.

The rotation of +10.21° indicates this meso compound is contaminated with 23% of (R,R)-(+)-5 having rotation +44.01°.

Anal. Calcd. for $C_9H_{13}NO_2$: C, 64.65; H, 7.84; N, 8.38.
Found: C, 64.45; H, 7.99; N, 8.44.

Example 34

(R,R)-α,α'-Dimethyl-2,6-pyridine dimethanol
(Compound (R,R)-5)

The diacetate of compound (R,R)-5 was hydrolyzed with sodium hydroxide in anhydrous methanol as described for compound (R,R) 3 above. To prevent reacetylation of the hydrolyzed diol it was again necessary to adjust the mixture to pH 6.5 with methanolic HCl before evaporating the methanol. 0.450 g (85%) of compound (R,R)-5 were isolated as a white microcrystalline solid.

M.P.: 62°-64° C.
$[\alpha]_D^{amb}$: +44.01° (c=2, acetone).

The $^1$H NMR spectrum was identical with that of the mixture of diol stereoisomers.

Anal. Calcd. for $C_9H_{13}NO_2$: C, 64.65; H, 7.84; N, 8.38.
Found: C, 64.66; H, 7.98; N, 8.38.

Example 35

Separation of
α,α',α''-trimethyl-1,3,5-benzenetrimethanol
Stereoisomers

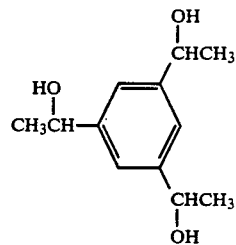

The triol was prepared by reduction of 1,3,5-triacetylbenzene. It was found to have very low solubility in benzene.

Because of the low solubility of the triol, it was expected that non-enzymatic esterification of partially esterified triols would become a significant, detrimental side reaction over long reaction times. Thus, the triol was chemically converted to the triacetate and then stereoselective hydrolysis was conducted with the enzyme.

The hydrolysis required 28 days in a buffer held near pH 7.4 by addition of aqueous base to consume the theoretical 0.5 mole of hydroxide using unsupported Amano P as the catalyst. No further change was observed upon stirring for an additional day. The characteristics of the products obtained are shown in Table 2 below.

TABLE 2

Specific Rotations of the Enzymatic Hydrolysis Products and Fully Hydrolyzed Triol Products in the Separation of the Stereoisomers of Tris-1,3,5-(1-hydroxyethyl)benzene

| stereochemical designation | number of acetate groups in enzymatic hydrolysis product | $[\alpha]_D^{25°}$ of enzymatic hydrolysis product | $[\alpha]_D^{21°}$ of the fully hydrolyzed triol |
|---|---|---|---|
| (R,R,R) | 0 | +95.50° | +95.50° |
| (S,S,S) | 3 | −173.25° | −94.10° |
| (R,S,S) | 2 | −114.75° | −32.10° |
| (R,R,S) | 1 | +14.50° | +32.31° |

Example 36

Preparation of the Stereoisomer Mixture of
α,α',α''-Trimethyl-1,3,5-benzenetrimethanol
(Compounds (S,S,S)-, (R,S,S)-, (S,R,R)-, and
(R,R,R)-7)

This mixture of stereoisomers was prepared from the poorly soluble 1,3,5-diacetylbenzene by reduction with sodium borohydride as described above for the α,α-dimethyl-1,4-benzenedimethanol stereoisomers.

The product was isolated as a very pale yellow solid that appeared as a single spot on TLC.

M.P.: 122°-126° C.

¹HNMR(CD₃COCD₃): 7.28 (s, 3 H); 4.87 (q 68.54; H, 8.63.

Anal. Calcd. for C₁₂H₁₈O₃: C, 68.54; H, 8.63.
Found: C, 68.75; H, 8.85.

Example 37

Preparation of the Stereoisomer Mixture of α,α',α''-Trimethyl-1,3,5-benzenetrimethanol Triacetates To a 250 mL three-necked round bottom flask equipped with a magnetic stirrer and a dry nitrogen inlet was added 4.0 g (19.0 mmol) of the stereoisomer mixture of triols 7 mixed with 50 mL of dichloromethane. The solution was stirred and to it were added 8.74 g (85.6 mmol) of acetic anhydride, 8.67 g (85.7 mmol) of triethylamine, and 0.25 g (2.0 mmol) of 4-(N,N-dimethylamino)pyridine (DMAP).

The partially soluble triol was completely dissolved after about 0.5 hrs., and after 2 hrs., TLC analysis showed only one spot at an Rf much higher than that of the triol. The reaction was quenched by cooling the flask in an ice water bath then slowly adding 50 mL of water. The phases were separated and the organic phase was extracted with 3×50 mL of aqueous citric acid solution then 3×50 mL of saturated aqueous sodium bicarbonate solution, and finally, with 2×100 mL of water.

After drying over magnesium sulfate, the solvent was evaporated to yield a dark yellow oil which was passed through a 4 in bed of silica gel eluted with 1:1 hexane/ethyl acetate to provide 5.88 g (92%) of a light yellow oil.

¹HNMR(CDCl₃): delta 7.26 (s, 3 H); 5.89 (q,j=6.6, 3 H); 2.09 (s, 9 H); 1.53 (d, J=6.6, 9 H).

The oil was used in the next step without additional characterization.

Example 38

Separation of the Stereoisomers of α,α',α''-Trimethyl-1,3,5-benzenetrimethanol (Compound 7)

To a 500 mL three-necked round bottom flask equipped with a magnetic stirrer and a pH electrode was added 5.86 g (17.42 mmol) of the stereoisomer mixture of α,α'α''-trimethyl-1,3,5-benzenetrimethanol triacetate dissolved in 20 mL of benzene. To this was added 100 mL of a 0.1M potassium phosphate buffer that had been adjusted to pH 7.8 followed by 0.600 g of unsupported Amano P lipase catalyst.

The yellow reaction mixture was stirred at room temperature for 672 hours (28 days) while maintaining the pH between 7.5 and 8.2 by daily additions of 1.0M aqueous sodium hydroxide solution. After 672 hours, 25.7 mL of the theoretical 26.1 mL of base had been added and the pH ceased to change over the next 24 hrs.

The mixture was diluted with 300 mL of dichloromethane then stirred rapidly. The resulting emulsion was broken by gravity filtration through a glass fiber filter. The phases were separated and the organic phase was dried with sodium sulfate then the solvent removed and the resulting light yellow oil subjected to flash chromatography on a 6 in bed of 60/60 Angstrom silica gel eluted with 1:2 hexane/ethyl acetate to give three fractions.

Example 39

Isolation of (S,S,S)-α,α'α''-Trimethyl-1,3,5-benzenetrimethanol Triacetate

The first fraction (highest Rf) comprises 0.91 g of a colorless oil accounting for 15.5% of the starting triacetate. It was shown to be the triacetate of compound (S,S,S)-7.

$[\alpha]_D^{amb}$: −173.25° (c=2, acetone).

The ¹H NMR spectrum was identical with that described above for the stereoisomer mixture of triacetates.

Anal. Calcd. for C₁₈H₂₄O₆: C, 64.28; H 7.19.
Found: C, 64.64; H, 7.38.

Example 40

Isolation of (R,S,S)-α,α'-Trimethyl-1,3,5-benzenetrimethanol Diacetate

The second fraction comprised 1.33 g of a colorless oil accounting for 25.9% of the starting triacetate. It was shown to be the diacetate of compound (R,S,S)-7.

$[\alpha]_D^{amb}$: −114.75° (c=2, acetone).

¹HNMR(CD₃COCD₃): delta 7.29 (d,J=1.5, 2 H), 7.22 (d,j=1.5, 1 H) 5.87 (q, j=6.6 Hz, 2 H); 4.87 (q, j=6.4, 1 H); 2.55–2.70 (br m, 1 H); 2.06 (s 6 H), 1.52 (d, j=6.6 Hz, 6 H); 1.48 (d, j=6.6 Hz, 6 H); 1.48 (d, j=6.4, 3 H).

Anal. Calcd. for C₁₆H₂₂O₅: C, 65.28; H, 7.53.
Found: C, 65.27; H, 7.64.

Example 41

Isolation of (R,R,S)-α,α'-Trimethyl-1,3,5-benzenetrimethanol Monoacetate

The third fraction comprised 1.41 g of a very pale yellow oil accounting for 32.0% of the starting triacetate it was shown to be the monoacetate of compound (R,R,S)-7.

$[\alpha]_D^{amb}$: 14.50° (c=2.2, acetone).

¹HNMR(CD₃COCD₃): delta 7.28(d,j=1.4 1 H), 7.23 (d,j=1.4 Hz, 2 H), 5.84 (q,j=6.6 Hz, 1 H), 4,84 (q,j=6.4, 2 H), 2.55–2.70 (br m, 3 H, 7.99.

Anal. Calcd. for C₁₄H₂₀O₄: C 66.64; H, 7.99.
Found: C, 66.57; H, 8.10.

Example 42

Isolation of (R,R,R)-α,α',α''-trimethyl-1,3,5-benzenetrimethanol (Compound (R,R,R)-7)

The aqueous phase was reduced to near dryness by evaporation of the water then was extracted with 3×50 mL of acetone. The acetone was evaporated to provide 0.605 g of an off white solid that accounted for 21.4% of the starting triacetate.

Recrystallization from 3:1 hexane/ethyl acetate yielded 0.51 g of rectangular plate crystals which were shown to be compound (R,R,R)-7.

$[\alpha]_D^{25}$: +95.50° (c=2, acetone).

The ¹H NMR spectrum was identical with that described above for the triol stereoisomer mixture.

Anal. Calcd. for C₁₂H₁₈O₃: C, 68.54; H, 8.63.
Found: C, 68.75; H, 8.85.

Example 43

(R,R,S)-α,α',α"-Trimethyl-1,3,5-benzenetrimethanol (Compound (R,R,S)-7))

The monoacetate of compound (R,R,S)-7 was hydrolyzed by treatment with sodium hydroxide in absolute methanol as described for the mono- and diacetates of α,α'-dimethyl-1,3-benzendimethanol (compound 4) above. Again, to prevent re-acetylation of the alcohols, it was necessary to neutralize the reaction mixture to pH 6.5 with methanolic HCl before evaporation of the methanol.

The (R,R,S) triol was isolated as a white microcrystalline powder, 0.45 g (90%).

M.P.: 123°-125° C.

$[\alpha]_D^{amb}$: +32.31° (c=2, acetone).

The $^1$H NMR spectrum was identical with that of the mixture of triol stereoisomers.

Anal. Calcd. for $C_{12}H_{18}O_3$: C, 68.54; H, 8.63.
Found: C, 68.69; H, 8.78.

Example 44

(R,S,S)-α,α',α"-Trimethyl-1,3-benzenetrimethanol (Compound (R,S,S)-7

The diacetate of compound (R,S,S) 7 was hydrolyzed with sodium hydroxide in anhydrous methanol as described for the mono- and diacetates of compound 4 above. To prevent reacetylation of the hydrolyzed alcohols it was necessary to adjust the mixture to pH 6.5 with methanolic HCl before evaporating the methanol.

The (R,S,S) triol was isolated as a white, microcrystalline powder, 0.47 g (87%).

M.P.: 123°-125° C.

$[\alpha]_D^{25°}$: -32.10° (c=2, acetone).

The $^1$H NMR spectrum was identical with that of the mixture of triol stereoisomers.

Anal. Calcd. for $C_{12}H_{18}O_3$: C, 68.54, H, 8.63.
Found: C, 68.39; H, 8.71.

Example 45

(S,S,S)-α,α',α"-Trimethyl-1,3-benzenetrimethanol (Compound (S,S,S)-7

The triacetate of compound (S,S,S)-7 was hydrolyzed with sodium hydroxide in anhydrous methanol as described for the mono- and diacetates of 4 above. To prevent reacetylation of the hydrolyzed alcohols it was necessary to adjust the mixture to pH 6.5 with methanolic HCl before evaporating the methanol.

The (S,S,S) triol was isolated as rectangular plates, 0.384 g (87%).

M.P.: 128°-129° C.

$[\alpha]_D^{amb}$: -94.10° (c=2, acetone).

The $^1$HNMR spectrum was identical with that of the mixture of triol stereoisomers.

Anal. Calcd. for $C_{12}H_{18}O_3$: C, 68.54; H, 8.63.
Found: C, 68.57; H, 8.45.

The invention now being fully described, it will be apparent to one of ordinary skill in the art that many changes and modifications can be made hereto without departing from the spirit or scope of the invention as set forth herein.

We claim:

1. A method of separating stereoisomers of a compound of the formula

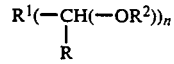

wherein
n is 2 or 3;
R and $R^1$ are different from one another and are selected from the group consisting of $(C_1-C_{20})$ alkyl, $(C_2-C_{20})$ alkenyl, $C_2-C_{20})$ alkynyl, $(C_3-C_{22})$ cycloalkyl, $(C_6-C_{22})$ aryl, said alkyl, alkenyl, alkynyl, cycloalkyl and aryl further including an atom selected from the group consisting of N, O and S in the ring or chain, said alkyl, alkenyl and alkynyl further including a substituent selected from the group consisting of $(C_1-C_4)$ alkyl and halogen, and said cycloalkyl and aryl further including a substituent selected from the group consisting of $(C_1-C_{10})$ alkoxy, aryloxy, halogen, $NO_2$ and $NHCOR^4$ wherein $R^4$ is selected from the group consisting of $(C_1-C_6)$ alkyl, $(C_2-C_6)$ alkenyl, $(C_2-C_6)$ alkynyl and $(C_6-C_{10})$ aryl; and
$R^2$ is selected from the group consisting of $-COR^7$;
said method comprising reacting a stereochemical mixture of a secondary alcohol of the formula $R^1(-HC(-R)(-OH))_n$, wherein n, R and $R^1$ are as defined above with an $R^7$ acyl anhydride or an activated $R^6OCOR^7$ ester, wherein $R^6$ is $(C_1-C_4)$ alkyl, $CF_3CH_2$, $CCl_3CH_2$, nitrophenyl or chlorophenyl, and $R^7$ is $(C_1-C_5)$alkyl, $CH_2Cl$ or $CH_2CN$, in the presence of an lipoprotein lipase capable of stereoselectively acylating an (R) or (S) site of a secondary alcohol, said alcohol mixture, anhydride or activated ester and lipoprotein lipase being provided in a medium, in proportions and under conditions effective to form (R) or (S) site acyl esters, respectively, of the secondary alcohol; and
if an (R) site is acylated and n is 2, separating the (S,S) secondary alcohol, (R,S) monoacyl ester and (R,R) diacyl ester from one another and the reaction medium;
if an (R) site is acylated and n is 3, separating the (S,S,S) secondary alcohol, (R,S,S) monoacyl ester, (R,R,S) diacyl ester and (R,R,R) triacyl ester from one another and the reaction medium;
if an (S) site is acylated and n is 2, separating the (R,R) secondary alcohol, (R,S) monoacyl ester and (S,S) diacyl ester from one another and the reaction medium; and
if an (S) site is acylated and n is 3, separating the (R,R,R) secondary alcohol, (R,R,S) monoacyl ester, (R,S,S) diacyl ester and (S,S,S) triacyl ester from one another and the reaction medium.

2. The method of claim 1, wherein
the separation step employs at least one technique selected from the group consisting of extraction, fractional distillation, chromatography, and temperature-controlled precipitation.

3. The method of claim 1, wherein
the acyl anhydride is acetic anhydride; and
the reaction medium is an anhydrous or nearly anhydrous organic liquid.

4. The method of claim 1, wherein
the enzyme is selected from Pseudomonas and porcine pancreatic lipases.

5. The method of claim 1, further comprising
separating the lipoprotein lipase from the reaction medium prior to separating the stereoisomers.

6. The method of claim 1, further comprising
separately hydrolyzing at least one of the monoacylated stereoisomer, the diacylated stereoisomer and, if n is 3, the triacylester stereoisomer in an aqueous or partially aqueous medium to obtain the corresponding unacylated stereoisomers of the alcohol; and
separating the stereoisomers of the alcohol from their hydrolysis media.

7. The method of claim 1, further comprising
separately reacting partially separated unacylated, monoacylated and diacylated alcohols with further acyl anhydride or ester and lipoprotein lipase in a medium, in proportions and under conditions effective to form further monoacylated, diacylated, and, if n is 3, triacylated stereoisomers; and
separating the alcohol, the monoacyl alcohol ester, the diacyl alcohol ester and, if n is 3, triacyl alcohol ester stereoisomers from one another and from the reaction medium.

8. The method of claim 1, wherein the lipoprotein lipase is provided on a solid support, and further wherein the alcohol mixture and the acyl anhydride or activated ester are reacted in the presence of the solid supported lipoprotein lipase.

9. A method of separating stereoisomers of a compound of the formula

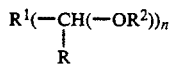

wherein
n is 2 or 3;
R and $R^1$ are different from one another and are selected from the group consisting of ($C_1$-$C_{20}$) alkyl, ($C_2$-$C_{20}$) alkenyl, ($C_2$-$C_{20}$) alkynyl, ($C_3$-$C_{22}$) cycloalkyl, ($C_6$-$C_{22}$) aryl, said alkyl, alkenyl, alkynyl, cycloalkyl and aryl further including an atom selected from the group consisting of N, O and S in the ring or chain, said alkyl, alkenyl and alkynyl further including a substituent selected from the group consisting of ($C_1$-$C_4$) alkyl and halogen, and said cycloalkyl and aryl further including a substitutent selected from the group consisting of ($C_1$-$C_{10}$) alkoxy, aryloxy, halogen, $NO_2$ and $NHCOR^4$ wherein $R^4$ is selected from the group consisting of ($C_1$-$C_6$) alkyl, ($C_2$-$C_6$) alkenyl, ($C_2$-$C_6$) alkynyl and ($C_6$-$C_{10}$) aryl; and
$R^2$ is ($C_1$-$C_7$) acyl;
said method comprising reacting a stereochemical mixture of esters of the formula $R^1$(—HC(—R)-(—OR^2))_n$, wherein n, $R^1$ and $R^2$ are as defined above with a lipoprotein lipase capable of stereoselectively deacylating an (R) or (S) site of a secondary alcohol, said ester and lipoprotein lipase being provided in an aqueous medium, in proportions and under conditions effective to form (R) or (S) site deacylated isomers, respectively, of the secondary alcohol; and if an (R) site is deacylated and n is 2, separating the (R,R) free alcohol, (R,S) monoacyl ester and (S,S) diacyl ester from one another and the reaction medium;

if an (R) site is deacylated and n is 3, separating the (R,R,R) free alcohol, (R,R,S) monoacyl ester, (R,S,S) diacyl ester and (S,S,S) triacyl ester from one another and the reaction medium;

if an (S) site is deacylated and n is 2, separating the (S,S) free alcohol, (R,S) monoacyl ester and (R,R) diacyl ester from one another and the reaction medium; and if an (S) site is acylated and n is 3, separating the (S,S,S) free alcohol, (R,S,S) monoacyl ester, (R,R,S) diacyl ester and (R,R,R) triacyl ester from one another and the reaction medium.

10. The method of claim 9, wherein
the separation step employs at least one technique selected from the group consisting of extraction, fractional distillation, chromatography, and temperature controlled fractional precipitation.

11. The method of claim 9, further comprising
separately reacting fractions comprising partially separated stereoisomers of the alcohol with a lipoprotein lipase capable of selectively deacylating the (R) or (S) site of an ester of a secondary alcohol in an aqueous medium, in proportions and under conditions effective to form the free alcohol, the diacyl ester, the monoacyl ester and, if n is 3, the triacylester stereoisomers of the alcohol; and
separating triacyl ester, diacyl ester, the monoacyl ester and free alcohol from one another and from their reaction medium.

12. The method of claim 9 wherein
the pH of the medium is maintained at about 6.5 to 8.

13. The method of claim 9, wherein
the lipoprotein lipase is provided on a solid support; and
the fully acylated compound is reacted in the presence of the solid supported lipoprotein lipase.

14. The method of claim 13, further comprising
separating the lipoprotein lipase from the reaction medium prior to separating the stereoisomers of the alcohol.

15. The method of claim 9, wherein
the lipoprotein lipase is selected from the group consisting of Pseudomonas and porcine pancreatic lipases.

16. The method of claim 9, further comprising
separately hydrolyzing at least one of the diacyl ester, the monoacyl ester and, if n is 3, the triacyl ester of the alcohol in a medium and under conditions effective to form the free alcohols; and
separating each stereoisomer from its medium.

* * * * *